(12) United States Patent
Harris et al.

(10) Patent No.: US 7,635,562 B2
(45) Date of Patent: Dec. 22, 2009

(54) METHODS AND DEVICES FOR NUCLEIC ACID SEQUENCE DETERMINATION

(75) Inventors: Timothy Harris, Ocean County, NJ (US); Philip Richard Buzby, Brockton, MA (US); Mirna Jarosz, Boston, MA (US); James Joseph DiMeo, Needham, MA (US); Jaime Gill, Marshfield Hills, MA (US)

(73) Assignee: Helicos BioSciences Corporation, Cambridge, MA (US)

( * ) Notice: Subject to any disclaimer, the term of this patent is extended or adjusted under 35 U.S.C. 154(b) by 29 days.

(21) Appl. No.: 11/137,928

(22) Filed: May 25, 2005

(65) Prior Publication Data

US 2006/0019276 A1    Jan. 26, 2006

Related U.S. Application Data

(60) Provisional application No. 60/574,389, filed on May 25, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| | | | |
|---|---|---|---|
| 3,996,345 A | 12/1976 | Ullman et al. |
| 4,119,368 A | 10/1978 | Yamazaki |
| 4,153,855 A | 5/1979 | Feingold |
| 4,344,064 A | 8/1982 | Bitler et al. |
| 4,351,760 A | 9/1982 | Khanna et al. |
| 4,683,195 A | 7/1987 | Mullis et al. |
| 4,683,202 A | 7/1987 | Mullis |
| 4,707,237 A | 11/1987 | Lepp et al. |
| 4,711,955 A | 12/1987 | Ward et al. |
| 4,725,677 A | 2/1988 | Koster et al. |
| 4,739,044 A | 4/1988 | Stabinsky |
| 4,757,141 A | 7/1988 | Fung et al. |
| 4,793,705 A | 12/1988 | Shera |
| 4,811,218 A | 3/1989 | Hunkapiller et al. |
| 4,863,849 A | 9/1989 | Melamede |
| 4,865,968 A | 9/1989 | Orgel et al. |
| 4,889,818 A | 12/1989 | Gelfand et al. |
| 4,942,124 A | 7/1990 | Church |
| 4,962,037 A | 10/1990 | Jett et al. |
| 4,971,903 A | 11/1990 | Hyman |
| 4,979,824 A | 12/1990 | Mathies et al. |
| 4,994,368 A | 2/1991 | Goodman et al. |
| 4,994,372 A | 2/1991 | Tabor et al. |
| 4,994,373 A | 2/1991 | Stavrianopoulos et al. |
| 5,085,562 A | 2/1992 | Van Lintel |
| 5,091,652 A | 2/1992 | Mathies et al. |
| 5,096,388 A | 3/1992 | Weinberg |
| 5,096,554 A | 3/1992 | Chin |
| 5,108,892 A | 4/1992 | Burke et al. |
| 5,112,736 A | 5/1992 | Caldwell et al. |
| RE34,069 E | 9/1992 | Koster et al. |
| 5,143,854 A | 9/1992 | Pirrung et al. |
| 5,167,784 A | 12/1992 | Noolandi |
| 5,171,132 A | 12/1992 | Miyazaki et al. |
| 5,198,540 A | 3/1993 | Koster |
| 5,209,834 A | 5/1993 | Shera |
| 5,224,843 A | 7/1993 | Van Lintel |
| 5,242,796 A | 9/1993 | Prober et al. |
| 5,242,797 A | 9/1993 | Hirschfeld |
| 5,258,506 A | 11/1993 | Urdea et al. |
| 5,259,737 A | 11/1993 | Kamisuki et al. |
| 5,260,433 A | 11/1993 | Engelhardt et al. |
| 5,265,327 A | 11/1993 | Faris et al. |
| 5,267,152 A | 11/1993 | Yang et al. |
| 5,302,509 A | 4/1994 | Cheeseman |
| 5,304,487 A | 4/1994 | Wilding et al. |
| 5,306,403 A | 4/1994 | Vo-Dinh |
| 5,336,062 A | 8/1994 | Richter |
| 5,360,523 A | 11/1994 | Middendorf et al. |
| 5,375,979 A | 12/1994 | Trah |
| 5,376,252 A | 12/1994 | Ekstrom et al. |
| 5,403,709 A | 4/1995 | Agrawal et al. |
| 5,405,747 A | 4/1995 | Jett et al. |
| 5,405,783 A | 4/1995 | Pirrung et al. |
| 5,409,811 A | 4/1995 | Tabor et al. |
| 5,424,186 A | 6/1995 | Fodor et al. |
| 5,436,149 A | 7/1995 | Barnes |
| 5,449,767 A | 9/1995 | Ward et al. |

(Continued)

FOREIGN PATENT DOCUMENTS

EP    0223618 A2    5/1987

(Continued)

OTHER PUBLICATIONS

Adam et al., "Individual genomes targeted in sequencing revolution", Nature, vol. 411, p. 402 (May 2001).

(Continued)

*Primary Examiner*—James Martinell
(74) *Attorney, Agent, or Firm*—Thomas Meyers; Adam Schoen; Brown Rudnick LLP

(57) ABSTRACT

Methods of the invention comprise methods and devices for nucleic acid sequence determination. Generally, the invention relates to preparing a substrate for sequencing a target nucleic acid.

13 Claims, 8 Drawing Sheets

U.S. PATENT DOCUMENTS

| | | | |
|---|---|---|---|
| 5,476,928 | A | 12/1995 | Ward et al. |
| 5,484,701 | A | 1/1996 | Cocuzza et al. |
| 5,492,806 | A | 2/1996 | Drmanac et al. |
| 5,514,256 | A | 5/1996 | Douthart et al. |
| 5,518,900 | A | 5/1996 | Nikiforov et al. |
| 5,525,464 | A | 6/1996 | Drmanac et al. |
| 5,529,465 | A | 6/1996 | Zengerle et al. |
| 5,534,125 | A | 7/1996 | Middendorf et al. |
| 5,547,839 | A | 8/1996 | Dower et al. |
| 5,547,859 | A | 8/1996 | Goodman et al. |
| 5,556,790 | A | 9/1996 | Pettit |
| 5,558,991 | A | 9/1996 | Trainor |
| 5,599,695 | A | 2/1997 | Pease et al. |
| 5,610,287 | A | 3/1997 | Nikiforov et al. |
| 5,631,734 | A | 5/1997 | Stern et al. |
| 5,632,957 | A | 5/1997 | Heller et al. |
| 5,654,149 | A | 8/1997 | Mendoza et al. |
| 5,659,171 | A | 8/1997 | Young et al. |
| 5,670,346 | A | 9/1997 | Reeve et al. |
| 5,674,716 | A | 10/1997 | Tabor et al. |
| 5,675,155 | A | 10/1997 | Pentoney, Jr. et al. |
| 5,688,648 | A | 11/1997 | Mathies et al. |
| 5,695,940 | A | 12/1997 | Drmanac et al. |
| 5,705,018 | A | 1/1998 | Hartley |
| 5,707,506 | A | 1/1998 | Douthart et al. |
| 5,710,628 | A | 1/1998 | Waterhouse et al. |
| 5,712,476 | A | 1/1998 | Renfrew et al. |
| 5,733,729 | A | 3/1998 | Lipshutz et al. |
| 5,741,640 | A | 4/1998 | Fuller |
| 5,741,644 | A | 4/1998 | Kambara et al. |
| 5,744,305 | A | 4/1998 | Fodor et al. |
| 5,744,312 | A | 4/1998 | Mamone et al. |
| 5,750,341 | A | 5/1998 | Macevicz |
| 5,753,788 | A | 5/1998 | Fodor et al. |
| 5,755,943 | A | 5/1998 | Middendorf et al. |
| 5,756,285 | A | 5/1998 | Fuller |
| 5,759,014 | A | 6/1998 | Van Lintel |
| 5,759,374 | A | 6/1998 | Takahashi et al. |
| 5,762,876 | A | 6/1998 | Lincoln et al. |
| 5,763,594 | A | 6/1998 | Hiatt et al. |
| 5,776,767 | A | 7/1998 | Stevens et al. |
| 5,776,782 | A | 7/1998 | Tsuji |
| 5,789,168 | A | 8/1998 | Leushner et al. |
| 5,795,722 | A | 8/1998 | Lacroix et al. |
| 5,795,782 | A | 8/1998 | Church et al. |
| 5,807,679 | A | 9/1998 | Kamb |
| 5,808,045 | A | 9/1998 | Hiatt et al. |
| 5,830,657 | A | 11/1998 | Leushner et al. |
| 5,831,070 | A | 11/1998 | Pease et al. |
| 5,832,165 | A | 11/1998 | Reichert et al. |
| 5,834,758 | A | 11/1998 | Trulson et al. |
| 5,836,750 | A | 11/1998 | Cabuz |
| 5,837,832 | A | 11/1998 | Chee et al. |
| 5,837,860 | A | 11/1998 | Anderson et al. |
| 5,846,396 | A | 12/1998 | Zanzucchi et al. |
| 5,846,727 | A | 12/1998 | Soper et al. |
| 5,853,979 | A | 12/1998 | Green et al. |
| 5,858,671 | A | 1/1999 | Jones |
| 5,861,287 | A | 1/1999 | Metzker et al. |
| 5,863,722 | A | 1/1999 | Brenner |
| 5,872,244 | A | 2/1999 | Hiatt et al. |
| 5,876,187 | A | 3/1999 | Forster et al. |
| 5,876,934 | A | 3/1999 | Duthie et al. |
| 5,882,904 | A | 3/1999 | Riedl et al. |
| 5,885,813 | A | 3/1999 | Davis et al. |
| 5,889,165 | A | 3/1999 | Fodor et al. |
| 5,902,723 | A | 5/1999 | Dower et al. |
| 5,908,755 | A | 6/1999 | Kumar et al. |
| 5,916,747 | A | 6/1999 | Gilchrist et al. |
| 5,922,591 | A | 7/1999 | Anderson et al. |
| 5,922,608 | A | 7/1999 | Farnsworth et al. |
| 5,928,906 | A | 7/1999 | Koster et al. |
| 5,928,919 | A | 7/1999 | Reha-Krantz et al. |
| 5,945,283 | A | 8/1999 | Kwok et al. |
| 5,945,284 | A | 8/1999 | Livak et al. |
| 5,945,312 | A | 8/1999 | Goodman et al. |
| 5,945,325 | A | 8/1999 | Arnold et al. |
| 5,948,614 | A | 9/1999 | Chatterjee |
| 5,952,174 | A | 9/1999 | Nikiforov et al. |
| 5,954,932 | A | 9/1999 | Takahashi et al. |
| 5,958,703 | A | 9/1999 | Dower et al. |
| 5,959,781 | A | 9/1999 | Kintz et al. |
| 5,959,837 | A | 9/1999 | Yu |
| 5,965,446 | A | 10/1999 | Ishikawa |
| 5,968,740 | A | 10/1999 | Fodor et al. |
| 5,974,164 | A | 10/1999 | Chee |
| 5,976,338 | A | 11/1999 | Fujita et al. |
| 5,976,842 | A | 11/1999 | Wurst |
| 5,981,186 | A | 11/1999 | Gabe et al. |
| 5,981,956 | A | 11/1999 | Stern |
| 5,994,058 | A | 11/1999 | Senapathy |
| 5,994,085 | A | 11/1999 | Cantor |
| 6,002,471 | A | 12/1999 | Quake |
| 6,005,663 | A | 12/1999 | Waterhouse et al. |
| 6,007,309 | A | 12/1999 | Hartley |
| 6,015,714 | A | 1/2000 | Baldarelli et al. |
| 6,017,702 | A | 1/2000 | Lee et al. |
| 6,018,041 | A | 1/2000 | Drmanac et al. |
| 6,020,457 | A | 2/2000 | Klimash et al. |
| 6,024,925 | A | 2/2000 | Little et al. |
| 6,025,136 | A | 2/2000 | Drmanac |
| 6,028,190 | A | 2/2000 | Mathies et al. |
| 6,030,782 | A | 2/2000 | Anderson et al. |
| 6,043,080 | A | 3/2000 | Lipshutz et al. |
| 6,046,005 | A | 4/2000 | Ju et al. |
| 6,049,380 | A | 4/2000 | Goodwin et al. |
| 6,051,380 | A | 4/2000 | Sosnowski et al. |
| 6,066,454 | A | 5/2000 | Lipshutz et al. |
| 6,071,394 | A | 6/2000 | Cheng et al. |
| 6,077,664 | A | 6/2000 | Slater et al. |
| 6,077,674 | A | 6/2000 | Schleifer et al. |
| 6,087,095 | A | 7/2000 | Rosenthal et al. |
| 6,087,099 | A | 7/2000 | Gupte et al. |
| 6,094,274 | A | 7/2000 | Yokoi |
| 6,107,032 | A | 8/2000 | Kilger et al. |
| 6,107,044 | A | 8/2000 | Nikiforov |
| 6,107,061 | A | 8/2000 | Johnson |
| 6,132,580 | A | 10/2000 | Mathies et al. |
| 6,133,436 | A | 10/2000 | Koster et al. |
| 6,136,212 | A | 10/2000 | Mastrangelo et al. |
| 6,136,962 | A | 10/2000 | Shi et al. |
| 6,140,053 | A | 10/2000 | Koster |
| 6,140,494 | A | 10/2000 | Hamilton et al. |
| 6,141,096 | A | 10/2000 | Stern et al. |
| 6,143,151 | A | 11/2000 | Middendorf et al. |
| 6,147,205 | A | 11/2000 | McGall et al. |
| 6,156,501 | A | 12/2000 | McGall et al. |
| 6,165,694 | A | 12/2000 | Liu |
| 6,177,249 | B1 | 1/2001 | Kwok et al. |
| 6,197,506 | B1 | 3/2001 | Fodor et al. |
| 6,197,595 | B1 | 3/2001 | Anderson et al. |
| 6,207,381 | B1 | 3/2001 | Larsson et al. |
| 6,207,960 | B1 | 3/2001 | Stern |
| 6,210,896 | B1 | 4/2001 | Chan |
| 6,214,246 | B1 | 4/2001 | Craighead |
| 6,214,987 | B1 | 4/2001 | Hiatt et al. |
| 6,221,592 | B1 | 4/2001 | Schwartz et al. |
| 6,221,654 | B1 | 4/2001 | Quake et al. |
| 6,225,052 | B1 | 5/2001 | Batz et al. |
| 6,225,062 | B1 | 5/2001 | Dunn et al. |
| 6,225,092 | B1 | 5/2001 | Kilger et al. |
| 6,225,109 | B1 | 5/2001 | Juncosa et al. |
| 6,225,567 | B1 | 5/2001 | Kester |
| 6,225,625 | B1 | 5/2001 | Pirrung et al. |

| | | |
|---|---|---|
| 6,228,593 B1 | 5/2001 | Lipshutz et al. |
| 6,232,075 B1 | 5/2001 | Williams |
| 6,232,103 B1 | 5/2001 | Short |
| 6,235,465 B1 | 5/2001 | Kolberg et al. |
| 6,235,473 B1 | 5/2001 | Friedman et al. |
| 6,242,180 B1 | 6/2001 | Chee |
| 6,242,528 B1 | 6/2001 | Clark et al. |
| 6,245,506 B1 | 6/2001 | Lauharn, Jr. et al. |
| 6,245,507 B1 | 6/2001 | Bogdanov |
| 6,245,518 B1 | 6/2001 | Baier |
| 6,251,610 B1 | 6/2001 | Gupte et al. |
| 6,255,083 B1 | 7/2001 | Williams |
| 6,255,475 B1 | 7/2001 | Kwiatkowski |
| 6,258,533 B1 | 7/2001 | Jones |
| 6,261,775 B1 | 7/2001 | Bastian et al. |
| 6,261,776 B1 | 7/2001 | Pirrung et al. |
| 6,261,848 B1 | 7/2001 | Anderson et al. |
| 6,262,838 B1 | 7/2001 | Montagu |
| 6,263,286 B1 | 7/2001 | Gilmanshin et al. |
| 6,265,155 B1 * | 7/2001 | Meade et al. ............... 435/6 |
| 6,268,152 B1 | 7/2001 | Fodor et al. |
| 6,268,219 B1 | 7/2001 | Mcbride et al. |
| 6,269,846 B1 | 8/2001 | Overbeck et al. |
| 6,270,644 B1 | 8/2001 | Mathies et al. |
| 6,270,961 B1 | 8/2001 | Drmanac |
| 6,274,320 B1 | 8/2001 | Rothberg et al. |
| 6,274,351 B1 | 8/2001 | Peponnet |
| 6,277,604 B1 | 8/2001 | Peponnet |
| 6,280,954 B1 | 8/2001 | Ulfendahl |
| 6,284,460 B1 | 9/2001 | Fodor et al. |
| 6,287,821 B1 | 9/2001 | Shi et al. |
| 6,294,336 B1 | 9/2001 | Boyce-Jacino et al. |
| 6,294,337 B1 | 9/2001 | Hayashizaki |
| 6,306,607 B2 | 10/2001 | Williams |
| 6,309,601 B1 | 10/2001 | Juncosa et al. |
| 6,309,701 B1 | 10/2001 | Barbera-Guillem |
| 6,309,824 B1 | 10/2001 | Drmanac |
| 6,309,836 B1 | 10/2001 | Kwiatowski |
| 6,309,886 B1 | 10/2001 | Ambrose et al. |
| 6,310,189 B1 | 10/2001 | Fodor et al. |
| 6,312,893 B1 | 11/2001 | Van Ness et al. |
| 6,316,191 B1 | 11/2001 | Drmanac et al. |
| 6,322,968 B1 | 11/2001 | Head et al. |
| 6,331,439 B1 | 12/2001 | Cherukuri et al. |
| 6,333,183 B1 | 12/2001 | Evans et al. |
| 6,335,824 B1 | 1/2002 | Overbeck |
| 6,337,185 B1 | 1/2002 | Asp et al. |
| 6,337,188 B1 | 1/2002 | Head et al. |
| 6,342,326 B1 | 1/2002 | Milton |
| 6,344,325 B1 | 2/2002 | Quake et al. |
| 6,346,379 B1 | 2/2002 | Gelfand et al. |
| 6,346,413 B1 | 2/2002 | Fodor et al. |
| 6,355,420 B1 | 3/2002 | Chan |
| 6,355,432 B1 | 3/2002 | Fodor et al. |
| 6,361,671 B1 | 3/2002 | Mathies et al. |
| 6,361,937 B1 | 3/2002 | Stryer |
| 6,368,562 B1 | 4/2002 | Yao |
| 6,368,699 B1 | 4/2002 | Gilbert et al. |
| 6,383,749 B2 | 5/2002 | Bochkariov et al. |
| 6,387,626 B1 | 5/2002 | Shi et al. |
| 6,395,232 B1 | 5/2002 | McBride |
| 6,395,559 B1 | 5/2002 | Swenson |
| 6,397,150 B1 | 5/2002 | Izmailov |
| 6,399,364 B1 | 6/2002 | Reeve et al. |
| 6,401,267 B1 | 6/2002 | Drmanac |
| 6,403,311 B1 | 6/2002 | Chan |
| 6,403,315 B1 | 6/2002 | Drmanac |
| 6,403,317 B1 | 6/2002 | Anderson |
| 6,403,320 B1 | 6/2002 | Read et al. |
| 6,403,957 B1 | 6/2002 | Fodor et al. |
| 6,404,907 B1 | 6/2002 | Gilchrist et al. |
| 6,406,893 B1 | 6/2002 | Knapp et al. |
| 6,407,858 B1 | 6/2002 | Montagu |
| 6,408,878 B2 | 6/2002 | Unger et al. |
| 6,416,952 B1 | 7/2002 | Pirrung et al. |
| 6,420,169 B1 | 7/2002 | Read et al. |
| 6,423,273 B1 | 7/2002 | O'Mara |
| 6,432,634 B1 | 8/2002 | Digby et al. |
| 6,436,641 B1 | 8/2002 | Izmailov |
| 6,436,646 B1 | 8/2002 | Nikiforov |
| 6,440,664 B1 | 8/2002 | Digby et al. |
| 6,440,722 B1 | 8/2002 | Knapp et al. |
| 6,444,106 B1 | 9/2002 | Mcbride et al. |
| 6,444,173 B1 | 9/2002 | Sjursen et al. |
| 6,444,424 B1 | 9/2002 | Chatterjee et al. |
| 6,444,461 B1 | 9/2002 | Knapp et al. |
| 6,447,724 B1 | 9/2002 | Jensen et al. |
| 6,448,090 B1 | 9/2002 | McBride |
| 6,451,536 B1 | 9/2002 | Fodor et al. |
| 6,479,267 B1 | 11/2002 | Davis et al. |
| 6,485,690 B1 | 11/2002 | Pfost et al. |
| 6,485,909 B1 | 11/2002 | Hong et al. |
| 6,485,944 B1 | 11/2002 | Church et al. |
| 6,495,363 B2 | 12/2002 | Bogdanov |
| 6,506,560 B1 | 1/2003 | Hughes et al. |
| 6,511,803 B1 | 1/2003 | Church et al. |
| 6,514,706 B1 | 2/2003 | Von Kalle et al. |
| 6,521,428 B1 | 2/2003 | Senapathy |
| 6,524,829 B1 | 2/2003 | Seeger |
| 6,528,258 B1 | 3/2003 | Russell |
| 6,528,288 B2 | 3/2003 | Senapathy |
| 6,537,755 B1 | 3/2003 | Drmanac |
| 6,537,757 B1 | 3/2003 | Langmore et al. |
| 6,546,340 B2 | 4/2003 | Lipshutz et al. |
| 6,551,784 B2 | 4/2003 | Fodor et al. |
| 6,551,817 B2 | 4/2003 | Besemer et al. |
| 6,554,987 B1 | 4/2003 | Gilchrist et al. |
| 6,555,349 B1 | 4/2003 | O'Donnell |
| 6,558,945 B1 | 5/2003 | Kao |
| 6,562,566 B1 | 5/2003 | Hoheisel |
| 6,566,059 B1 | 5/2003 | Stanton, Jr. et al. |
| 6,566,515 B1 | 5/2003 | McGall et al. |
| 6,573,047 B1 | 6/2003 | Hung et al. |
| 6,573,374 B1 | 6/2003 | Muehleger et al. |
| 6,576,424 B2 | 6/2003 | Fodor et al. |
| 6,576,425 B2 | 6/2003 | McGall et al. |
| 6,579,704 B2 | 6/2003 | Short |
| 6,582,923 B2 | 6/2003 | Stanton, Jr. et al. |
| 6,585,939 B1 | 7/2003 | Dapprich |
| 6,607,888 B2 | 8/2003 | Schwartz et al. |
| 6,610,482 B1 | 8/2003 | Fodor et al. |
| 6,613,513 B1 | 9/2003 | Parce et al. |
| 6,623,928 B2 | 9/2003 | Van Ness et al. |
| 6,627,748 B1 | 9/2003 | Ju et al. |
| 6,632,655 B1 | 10/2003 | Mehta et al. |
| 6,642,001 B1 | 11/2003 | Bolk et al. |
| 6,664,079 B2 | 12/2003 | Ju et al. |
| 6,719,868 B1 | 4/2004 | Schueller et al. |
| 6,750,018 B2 | 6/2004 | Kambara et al. |
| 6,762,048 B2 | 7/2004 | Williams |
| 6,780,591 B2 | 8/2004 | Williams et al. |
| 6,783,938 B2 | 8/2004 | Nygren et al. |
| 6,787,308 B2 | 9/2004 | Balasubramanian et al. |
| 6,818,395 B1 | 11/2004 | Quake et al. |
| 6,908,736 B1 | 6/2005 | Densham |
| 6,911,345 B2 | 6/2005 | Quake et al. |
| 2001/0024790 A1 | 9/2001 | Kambara et al. |
| 2001/0044531 A1 | 11/2001 | McGall et al. |
| 2001/0046681 A1 | 11/2001 | Senapathy |
| 2002/0009744 A1 | 1/2002 | Bogdanov |
| 2002/0012910 A1 | 1/2002 | Weiss et al. |
| 2002/0015961 A1 | 2/2002 | Kwiatkowski |
| 2002/0025529 A1 | 2/2002 | Quake et al. |
| 2002/0032320 A1 | 3/2002 | Burgess et al. |
| 2002/0034792 A1 | 3/2002 | Kilger et al. |
| 2002/0039738 A1 | 4/2002 | Williams et al. |

| | | |
|---|---|---|
| 2002/0042112 A1 | 4/2002 | Koster et al. |
| 2002/0045182 A1 | 4/2002 | Singh et al. |
| 2002/0051992 A1 | 5/2002 | Bridgham et al. |
| 2002/0053532 A1 | 5/2002 | Quake et al. |
| 2002/0061529 A1 | 5/2002 | Bridgham et al. |
| 2002/0072055 A1 | 6/2002 | Jones |
| 2002/0086318 A1 | 7/2002 | Manalis et al. |
| 2002/0102586 A1 | 8/2002 | Ju et al. |
| 2002/0102595 A1 | 8/2002 | Davis |
| 2002/0106673 A1 | 8/2002 | Drmanac et al. |
| 2002/0115076 A1 | 8/2002 | Williams |
| 2002/0115092 A1 | 8/2002 | Rebek, Jr. |
| 2002/0119484 A1 | 8/2002 | Weidenhammer et al. |
| 2002/0123046 A1 | 9/2002 | Smith et al. |
| 2002/0137046 A1 | 9/2002 | Koster |
| 2002/0137052 A1 | 9/2002 | Bridgham et al. |
| 2002/0137062 A1 | 9/2002 | Williams et al. |
| 2002/0138205 A1 | 9/2002 | Miller et al. |
| 2002/0142329 A1 | 10/2002 | Matray et al. |
| 2002/0142333 A1 | 10/2002 | Gelfand et al. |
| 2002/0146704 A1 | 10/2002 | Head et al. |
| 2002/0146726 A1 | 10/2002 | Matray et al. |
| 2002/0150903 A1 | 10/2002 | Koster |
| 2002/0150938 A1 | 10/2002 | Kneipp et al. |
| 2002/0164629 A1 | 11/2002 | Quake et al. |
| 2002/0168642 A1 | 11/2002 | Drukier |
| 2002/0168678 A1 | 11/2002 | Williams et al. |
| 2002/0172948 A1 | 11/2002 | Perlin |
| 2002/0177129 A1 | 11/2002 | Paabo et al. |
| 2002/0182601 A1 | 12/2002 | Sampson et al. |
| 2002/0192661 A1 | 12/2002 | Paabo et al. |
| 2002/0192662 A1 | 12/2002 | Boyce-Jacino et al. |
| 2002/0192691 A1 | 12/2002 | Drmanac |
| 2002/0197618 A1 | 12/2002 | Sampson |
| 2003/0003272 A1 | 1/2003 | Laguitton |
| 2003/0003498 A1 | 1/2003 | Digby et al. |
| 2003/0008285 A1 | 1/2003 | Fischer |
| 2003/0008413 A1 | 1/2003 | Kim et al. |
| 2003/0017461 A1 | 1/2003 | Singh et al. |
| 2003/0022207 A1 | 1/2003 | Balasubramanian et al. |
| 2003/0027140 A1 | 2/2003 | Ju et al. |
| 2003/0036080 A1 | 2/2003 | Jensen et al. |
| 2003/0044778 A1 | 3/2003 | Goelet et al. |
| 2003/0044779 A1 | 3/2003 | Goelet et al. |
| 2003/0044781 A1 | 3/2003 | Korlach et al. |
| 2003/0044816 A1 | 3/2003 | Denison et al. |
| 2003/0054181 A1 | 3/2003 | Swerdlow et al. |
| 2003/0054361 A1 | 3/2003 | Heller |
| 2003/0058440 A1 | 3/2003 | Scott et al. |
| 2003/0058799 A1 | 3/2003 | Yamakawa et al. |
| 2003/0059778 A1 | 3/2003 | Berlin et al. |
| 2003/0060431 A1 | 3/2003 | Simmonds et al. |
| 2003/0064366 A1 | 4/2003 | Hardin et al. |
| 2003/0064398 A1 | 4/2003 | Barnes |
| 2003/0064483 A1 | 4/2003 | Shaw et al. |
| 2003/0082618 A1* | 5/2003 | Li et al. .......... 435/6 |
| 2003/0087237 A1 | 5/2003 | Hong et al. |
| 2003/0087300 A1 | 5/2003 | Knapp et al. |
| 2003/0092005 A1 | 5/2003 | Levene et al. |
| 2003/0092007 A1 | 5/2003 | Gibbs et al. |
| 2003/0096258 A1 | 5/2003 | Fu et al. |
| 2003/0100006 A1 | 5/2003 | Senapathy |
| 2003/0104437 A1 | 6/2003 | Barnes et al. |
| 2003/0104466 A1 | 6/2003 | Knapp et al. |
| 2003/0108867 A1 | 6/2003 | Chee et al. |
| 2003/0138809 A1 | 7/2003 | Williams et al. |
| 2003/0148344 A1 | 8/2003 | Rothberg et al. |
| 2003/0148360 A1 | 8/2003 | Guire et al. |
| 2003/0162213 A1 | 8/2003 | Fuller et al. |
| 2003/0186227 A1 | 10/2003 | Balasubramanian et al. |
| 2003/0186255 A1 | 10/2003 | Williams et al. |
| 2003/0190627 A1 | 10/2003 | Zhao et al. |
| 2003/0190647 A1 | 10/2003 | Odera |
| 2003/0190660 A1 | 10/2003 | Lowe et al. |
| 2003/0190663 A1 | 10/2003 | Yang et al. |
| 2003/0194722 A1 | 10/2003 | Odedra et al. |
| 2003/0194740 A1 | 10/2003 | Williams |
| 2003/0215862 A1 | 11/2003 | Parce et al. |
| 2003/0215891 A1 | 11/2003 | Bickel et al. |
| 2004/0009487 A1 | 1/2004 | Kadushin et al. |
| 2004/0014096 A1 | 1/2004 | Anderson et al. |
| 2004/0029115 A9 | 2/2004 | Dower et al. |
| 2004/0038206 A1 | 2/2004 | Zhang et al. |
| 2004/0054162 A1 | 3/2004 | Hanna |
| 2004/0091903 A1 | 5/2004 | Balasubramanian et al. |
| 2004/0106110 A1 | 6/2004 | Balasubramanian et al. |
| 2004/0126765 A1 | 7/2004 | Adams |
| 2004/0126770 A1 | 7/2004 | Kumar et al. |
| 2005/0014175 A1 | 1/2005 | Quake |
| 2005/0100932 A1 | 5/2005 | Lapidus et al. |
| 2005/0147992 A1 | 7/2005 | Quake et al. |
| 2005/0170367 A1 | 8/2005 | Quake et al. |
| 2005/0239085 A1 | 10/2005 | Buzby et al. |

FOREIGN PATENT DOCUMENTS

| | | |
|---|---|---|
| EP | 0579997 A1 | 1/1994 |
| EP | 0706004 A2 | 4/1996 |
| EP | 0779436 A2 | 6/1997 |
| EP | 0845603 A1 | 6/1998 |
| EP | 0932700 B1 | 8/1999 |
| EP | 0946752 B1 | 10/1999 |
| EP | 0955085 A2 | 11/1999 |
| EP | 0999055 A2 | 5/2000 |
| EP | 0706004 B1 | 8/2003 |
| GB | 2155152 A | 9/1985 |
| GB | 2308460 A | 6/1997 |
| GB | 2400518 A | 10/2004 |
| SE | 9500589 | 2/1995 |
| WO | 89/03432 A1 | 4/1989 |
| WO | 89/09283 A1 | 10/1989 |
| WO | 90/13666 A1 | 11/1990 |
| WO | 90/15070 A1 | 12/1990 |
| WO | 91/06678 A1 | 5/1991 |
| WO | 92/10092 A1 | 6/1992 |
| WO | 92/10587 A1 | 6/1992 |
| WO | 93/05183 A1 | 3/1993 |
| WO | 93/06121 A1 | 4/1993 |
| WO | 93/21340 A1 | 10/1993 |
| WO | 95/12608 A1 | 5/1995 |
| WO | 95/27080 A1 | 10/1995 |
| WO | 96/04547 A1 | 2/1996 |
| WO | 96/12014 A1 | 4/1996 |
| WO | 96/12039 A1 | 4/1996 |
| WO | 96/27025 A1 | 9/1996 |
| WO | 97/02488 A1 | 1/1997 |
| WO | 97/22076 A1 | 6/1997 |
| WO | 97/23650 A2 | 7/1997 |
| WO | 97/37041 A2 | 10/1997 |
| WO | 97/39150 A1 | 10/1997 |
| WO | 97/40184 A1 | 10/1997 |
| WO | 97/41258 A1 | 11/1997 |
| WO | 97/41259 A1 | 11/1997 |
| WO | 97/42348 A1 | 11/1997 |
| WO | 98/00708 A1 | 1/1998 |
| WO | 98/02575 A1 | 1/1998 |
| WO | 98/03684 A1 | 1/1998 |
| WO | 98/07069 A1 | 2/1998 |
| WO | 98/08978 A1 | 3/1998 |
| WO | 98/13523 A1 | 4/1998 |
| WO | 98/20019 A1 | 5/1998 |
| WO | 98/20020 A2 | 5/1998 |
| WO | 98/20166 A2 | 5/1998 |
| WO | 98/21361 A1 | 5/1998 |
| WO | 98/27228 A1 | 6/1998 |
| WO | 98/28440 A1 | 7/1998 |

| | | | | | | |
|---|---|---|---|---|---|---|
| WO | 98/33939 | A1 | 8/1998 | WO | 01/57248 A2 | 8/2001 |
| WO | 98/40520 | A1 | 9/1998 | WO | 01/57249 A1 | 8/2001 |
| WO | 98/41650 | A2 | 9/1998 | WO | 01/61044 A1 | 8/2001 |
| WO | 98/41657 | A1 | 9/1998 | WO | 01/64838 A2 | 9/2001 |
| WO | 98/44152 | A1 | 10/1998 | WO | 01/75154 A2 | 10/2001 |
| WO | 98/45481 | A1 | 10/1998 | WO | 01/79536 A1 | 10/2001 |
| WO | 98/53300 | A2 | 11/1998 | WO | 01/85991 A2 | 11/2001 |
| WO | 98/54669 | A1 | 12/1998 | WO | 01/92284 A1 | 12/2001 |
| WO | 98/55593 | A1 | 12/1998 | WO | 01/96607 A2 | 12/2001 |
| WO | 99/01768 | A1 | 1/1999 | WO | 02/00343 A2 | 1/2002 |
| WO | 99/05221 | A1 | 2/1999 | WO | 02/02584 A1 | 1/2002 |
| WO | 99/05315 | A2 | 2/1999 | WO | 02/02795 A2 | 1/2002 |
| WO | 99/06422 | A2 | 2/1999 | WO | 02/02813 A2 | 1/2002 |
| WO | 99/09616 | A1 | 2/1999 | WO | 02/03305 A2 | 1/2002 |
| WO | 99/13109 | A1 | 3/1999 | WO | 02/04680 A2 | 1/2002 |
| WO | 99/13110 | A1 | 3/1999 | WO | 02/20836 A2 | 3/2002 |
| WO | 99/17093 | A1 | 4/1999 | WO | 02/20837 A2 | 3/2002 |
| WO | 99/19516 | A1 | 4/1999 | WO | 02/27032 A1 | 4/2002 |
| WO | 99/24797 | A1 | 5/1999 | WO | 02/29106 A2 | 4/2002 |
| WO | 99/27137 | A1 | 6/1999 | WO | 02/30486 A3 | 4/2002 |
| WO | 99/31278 | A1 | 6/1999 | WO | 02/35441 A2 | 5/2002 |
| WO | 99/37810 | A1 | 7/1999 | WO | 02/36832 A2 | 5/2002 |
| WO | 99/39001 | A2 | 8/1999 | WO | 02/44414 A2 | 6/2002 |
| WO | 99/40105 | A2 | 8/1999 | WO | 02/061126 A2 | 8/2002 |
| WO | 99/40223 | A1 | 8/1999 | WO | 02/061127 A2 | 8/2002 |
| WO | 99/41410 | A1 | 8/1999 | WO | 02/072779 A2 | 9/2002 |
| WO | 99/44045 | A1 | 9/1999 | WO | 02/072892 A1 | 9/2002 |
| WO | 99/45153 | A2 | 9/1999 | WO | 02/077694 A1 | 10/2002 |
| WO | 99/47539 | A1 | 9/1999 | WO | 02/079519 A1 | 10/2002 |
| WO | 99/47706 | A1 | 9/1999 | WO | 02/088381 A2 | 11/2002 |
| WO | 99/53423 | A1 | 10/1999 | WO | 02/088382 A2 | 11/2002 |
| WO | 99/57321 | A1 | 11/1999 | WO | 02/097113 A2 | 12/2002 |
| WO | 99/61888 | A2 | 12/1999 | WO | 02/099398 A1 | 12/2002 |
| WO | 99/64437 | A1 | 12/1999 | WO | 03/002767 A1 | 1/2003 |
| WO | 99/64840 | A1 | 12/1999 | WO | 03/016565 A2 | 2/2003 |
| WO | 99/65938 | A2 | 12/1999 | WO | 03/020895 A2 | 3/2003 |
| WO | 99/66076 | A1 | 12/1999 | WO | 03/020968 A2 | 3/2003 |
| WO | 99/66313 | A1 | 12/1999 | WO | 03/021010 A2 | 3/2003 |
| WO | 00/00637 | A2 | 1/2000 | WO | 03/031947 A2 | 4/2003 |
| WO | 00/06770 | A1 | 2/2000 | WO | 03/044678 A1 | 5/2003 |
| WO | 00/09753 | A1 | 2/2000 | WO | 03/048178 A2 | 6/2003 |
| WO | 00/11223 | A1 | 3/2000 | WO | 03/048991 A2 | 6/2003 |
| WO | 00/17397 | A1 | 3/2000 | WO | 03/062897 A1 | 7/2003 |
| WO | 00/26935 | A2 | 5/2000 | WO | 03/106642 A2 | 12/2003 |
| WO | 00/30591 | A1 | 6/2000 | WO | 2004/061119 A2 | 7/2004 |
| WO | 00/34523 | A1 | 6/2000 | WO | 2004/074503 A2 | 9/2004 |
| WO | 00/37680 | A1 | 6/2000 | WO | 2005/047523 A2 | 5/2005 |
| WO | 00/40750 | A1 | 7/2000 | WO | 2005/080605 A2 | 9/2005 |
| WO | 00/40758 | A2 | 7/2000 | | | |
| WO | 00/42223 | A1 | 7/2000 | | | |
| WO | 00/43540 | A1 | 7/2000 | | | |
| WO | 00/43752 | A1 | 7/2000 | | | |
| WO | 00/50642 | A1 | 8/2000 | | | |
| WO | 00/53805 | A1 | 9/2000 | | | |
| WO | 00/53812 | A2 | 9/2000 | | | |
| WO | 00/56937 | A2 | 9/2000 | | | |
| WO | 00/58507 | A1 | 10/2000 | | | |
| WO | 00/58516 | A2 | 10/2000 | | | |
| WO | 00/68410 | A1 | 11/2000 | | | |
| WO | 00/70073 | A1 | 11/2000 | | | |
| WO | 00/71755 | A2 | 11/2000 | | | |
| WO | 00/79007 | A1 | 12/2000 | | | |
| WO | 01/01025 | A3 | 1/2001 | | | |
| WO | 01/16375 | A2 | 3/2001 | | | |
| WO | 01/23610 | A2 | 4/2001 | | | |
| WO | 01/24937 | A2 | 4/2001 | | | |
| WO | 01/25480 | A2 | 4/2001 | | | |
| WO | 01/31055 | A2 | 5/2001 | | | |
| WO | 01/32930 | A1 | 5/2001 | | | |
| WO | 01/38574 | A1 | 5/2001 | | | |
| WO | 01/48184 | A2 | 5/2001 | | | |
| WO | WO01/38573 | | 5/2001 | | | |
| WO | 01/42496 | A2 | 6/2001 | | | |

OTHER PUBLICATIONS

Agrawal, S. et al., "Site Specific Functionalization of Oligodeoxynucleotides for Non-Radioactive Labelling", *Tetrahedron Letters*, vol. 31, No. 11, pp. 1543-1546 (1990).

Ambrose, W. et al., "Single Molecule Detection With Total Internal Reflection Excitation: Comparing Signal-to-Background and Total Signals in Different Geometries", *Cytometry*, vol. 36, pp. 224-231 (1999).

Amit, B. et al., "Photosensitive Protecting Groups of Amino Sugars and Their Use in Glycoside Synthesis ... Derivatives", *I. Org. Chem.*, 39(2):192-6 (1974).

Arndt-Jovin, D. et al., "Immunofluorescence Localization of Z-DNA in Chromosomes: Quantitation by Scanning Microphotometry and Computer-assisted Image Analysis", 1. *The Journal of Cell Biology*, vol. 101, pp. 1422-1433, (Oct. 1985).

Augustin, M.A., W. Ankenbauer, and B. Angerer, "Progress towards single-molecule sequencing: enzymatic synthesis of nucleotide-specifically labeled DNA." *Journal of Biotechnology*, 8(13): 289-301 (2001).

Axelrod, D., "Cell-Substrate Contacts Illuminated by Total Internal Reflection Fluorescence", 1. *The Journal of Cell Biology*, vol. 89, pp. 141-145, (Apr. 1981).

Axelrod, D. et al., "Total internal reflection fluorescent microscopy", *J Microscopy*, vol. 129, pp. 19-28, (1983).
Bai, X., et al., "Photocleavage of a 2-nitrobenzyl linker bridging a fluorophore to the 5' end of DNA." Proc Natl Acad Sci USA, 2003, vol. 100(2). p. 409-13.
Basche, T. et al., "Single Molecule Optical Detection, Imaging and Spectroscopy", Chs. 2 and 3, Weinheim:VCM, Germany (1997), pp. 191-243.
Beaucage, S. et al., "Advances in the Synthesis of Oligonucleotides by the Phosphoramidite Approach" *Tetrahedron*, 48:2223-2311 (1992).
Beese, L. et al., "Structure of DNA Polymerase I Klenow Fragment Bound to Duplex DNA", *Science*, 260:352-355 (1993).
Bennett et. al., "Solexa Sequencing chemistry can be applied to different platforms which will have common elements in detection and data processing", *Pharmacogenomics* 5(4), pp. 433-438, (2004).
Biesalski et al., "Preparation and Characterization of a Polyelectrolyte Monolayer Covalently Attached to a Planar Solid Surface", *Macromolecules* 111, 32, 2309-2316. Article was published on the web Mar. 10, 1999.
Black, D.L., "Protein diversity from alternating splicing: A challenge for bioinformatics and post genome biology", *Cell*, 2000. 103(3): p. 367-370.
Blattner, F.R., et al., "The Complete genome sequence of *Escherichia coli* K-12.", *Science*, 277: 1453-74 (1997).
Boles et. al., "High-Resolution Mapping of Carcinogen Binding Sites on DNA", *Biochemistry*, 1986, 25, 3039-3043.
Brakmann, S. and P. Nieckchen, "The large fragment of *Escherichia coli* DNA polymerase I can synthesize DNA exclusively from fluorescently labeled nucleotides." *Chembiochem*, 2(10): 773-777 (2001).
Brakmann et. al, "Optimal Enzymes for Single-Molecule Sequencing", *Current Pharmaceutical Biotechnology*, 5, pp. 119-126 (2004).
Braslavsky, I. et al., "Sequence information can be obtained from single DNA molecules", *PNAS*, vol. 100, No. 7, pp. 3960-3964 (Apr. 2003).
Braslavsky, I. et al., "Objective-type dark-field illumination for scattering from microbeads", *Applied Optics*, vol. 40, No. 31, pp. 5650-5657, (Nov. 2001).
Braslavsky, I. et al., "Single Molecule Measurements of DNA Polymerase Activity: A Step Towards Single Molecule Sequencing", *Biophys.* 1. *Abstracts*, p. 507A (2002).
Brechtel, R. et al., "Control of the electro osmotic flow by metal-salt-containing buffers", *J Chromatoraphy A*, vol. 716, pp. 97-105, (1995).
Bridgman, A. et al., "An improved method for the synthesis of mercurated dUTP. Enzymatic synthesis of Hg-labelled DNA of high molecular weight suitable for use in an image based DNA sequencing strategy", *DNA Seq.*, vol. 6, No. 4, pp. 199-209 (1996).
Bruggert, J. et al., "Microfabricated tools for nanoscience", *J. Micromech. Microeng.*, 3, pp. 161-167 (1993).
Bryzek, J. et al., "Micromachines on the march", *IEEE Spectrum*, vol. 31, No. 5, pp. 20-31, (1994).
Buchaillot, L. et al., "Silicon Nitride Thin Films Young's Modulus Determination by an Optical Non Destructive Method", *Jpn. J. Appl. Phys.*, vol. 36, pp. L794-L797, (Jun. 1997).
Burghardt, T. et al., "Total Internal Reflection Fluorescence Study of Energy Transfer in Surface-Adsorbed and Dissolved Bovine Serum Albumin", *Biochemistry*, vol. 22, pp. 979-985 (1983).
Burghardt, et al., "Total Internal Reflection/Fluorescence Photobleaching Recovery Study of Serum Albumin Adsorption Dynamics", *Biophys. Journal*, vol. 33, pp. 455-468 (Mar. 1981).
Butler, D. et al., "Draft data leave geneticists with a mountain still to climb", *Nature*, vol. 405, Issue 6782, pp. 984-985 (May 2000).
Canard, B., B. Cardona, and R.S. Sarfati, "Catalytic editing properties of DNA polymerases," Proc Natl Acad Sci USA, 92(24): p. 10859-63 (1995).
Canard, et al., "DNA polymerase fluorescent substrates with reversible 3'-tags", *Gene*, 148(1): 1-6 (1994).
Cheng et al., "High-speed DNA sequence analysis," *Prog. in Biochem. and Biophys.*, vol. 22, pp. 223-227 (1995), abstract only.
Chicurel, M., "Faster, better, cheaper genotyping", *Nature*, vol. 412, Issue 6847, pp. 580-582, (Aug. 2001).

Chidgeavadze et al., 2',3'-Dideoxy-3' aminonucleoside 5'-triphosphates are the terminators of DNA synthesis catalyzed by DNA polymerases, *Nuc. Acids Res.*, 12(3):1671-1686 (1984).
Chidgeavadze, Z. et al., "3'-Fluro-2',3'-dideoxyribonucleoside 5'-triphosphates: terminators of DNA synthesis", *FEBS Letters*, 183(2):275-278 (1985).
Chiu, D. et al., "Patterned deposition of cells and proteins onto surfaces by using three-dimensional microfluidic systems," *PNAS*, vol. 97, No. 6; pp. 2408-2413 (2000).
Chou et al., "A microfabricated device for sizing and sorting DNA molecules", Applied Sciences, Biophysics: Proc. Natl. Acad. Sci. USA 96, pp. 11-13 (1999).
Chou et al., "A Microfabricated Rotary Pump", Biomedical Microdevices. vol. 3: pp. 323-330 (2001).
Close, D. et al., "Ultraviolet Photobleaching of Free Radicals Created in γ-Irradiated Amino Acids", *Radiation Research*, vol. 53, pp. 349-357 (1973).
Cooper, J. et al., "Analysis of Fluorescence Energy Transfer in Duplex and Branched DNA Molecules", *Biochemistry*, vol. 29; pp. 9261-9268 (1990).
Crocker, J.C. and D.G. Grier, "Methods of digital video microscopy for colloidal studies." *Journal of Colloid and Interface Science*, 179(1): p. 298-310 (1996).
Dapprich, J., "Single-molecule DNA digestion by lambda-exonuclease." *Cytometry*, 36(3): p. 163-168 (1999).
Debenham, J.S., et al., "Two New Orthogonal Amine-Protecting Groups that can be Cleaved under Mild or Neutral Conditions." *Journal of the American Chemical Society*, 117(11): p. 3302-3 (1995).
Decher, G. et al. "Buildup of ultrathin multiplayer films by a self-assembly process: III. Consecutively alternating absorption of anionic and cationic polyelectrolytes on charged surfaces", *Thin Solid Films*, 210:831-835 (1992).
Decher G.;et al., "Fuzzy nanoassemblies : Toward layered polymeric multicomposites," *Science*, 277(5330): p. 1232-1237 (1997).
Delamarche, E. et al., "Patterned Delivery of Immunoglobulins to Surfaces Using Microfluidic Networks", *Science* 276:779-781 (1997).
Dickson et al., "Simultaneous Imaging of Individual Molecules aligned both parallel and perpendicular to the optic axis", *The American Physical Society*, vol. 81, No. 24, pp. 5322-5325 (1998).
Doktycz, M. et al., "Genosensors and Model Hybridization Studies", *Automation Technologies for Genome Characterization*, Ch. 10 T. Beugelsdijk (Ed), John Wiley & Sons, Inc., pp. 205-225 (1997).
Doublie, S. et al., "Crystal structure of a bacteriophage T7 DNA replication complex at 2.2 A resolution", *Nature*, vol. 391, pp. 251-258 (Jan. 1998).
Driscoll et al., "Atomic-Scale Imaging of DNA Using Scanning Tunneling Microscopy." *Nature*, 346(6281): p. 294-296 (1990).
Drmanac, R. et al., "Sequencing by hybridization: Towards an automated sequencing of one million M13 clones arrayed on membranes", *Electrophoresis*, 13:566-573 (1992).
Duffy et al., "Patterning Electroluminescence Materials with Feature Sizes as Small as 5 um Using Elastomeric Membranes as Masks for Dry Lift-Off," *Advanced Materials* vol. 11, No. 7, pp. 546-552 (1999).
Duffy et al., "Rapid prototyping of microfluidic switches in poly(dimethyl siloxane) and their acuation by electroosmotic flow," *J. Micromech. Microeng.*, vol., 9, pp. 211-217 (1999).
Duffy et al., "Rapid Prototyping of Microfluidic Systems in Poly(dimethylsiloxane)", *Analytical Chemistry*, vol. 70, No. 23, pp. 4974-4984 (1998).
Effenhauser et al., "Integrated capillary electrophoresis on Flexible silicone microdevices: Analysis of DNA restriction fragments and detection of single DNA molecules on microchips," *Anal. Chem.*, vol. 69, pp. 3451-3457 (1997).
Effenhauser et al., "Integrated chip-based capillary electrophoresis," *Electrophoresis*, vol, 18, pp. 2203-2213 (1997).
Eigen, M. et al., "Sorting single molecules: Application to diagnostics and evolutionary biotechnology", *PNAS*, vol. 91, pp. 5740-5747, (Jun. 1994).
Evangelista, R.A., et al. "Characterization of fluorescent nucleoside triphosphates by capillary electrophoresis with laser-induced fluorescence detection: action of alkaline phosphatase and DNA polymerase." *Analytical Biochemistry*, 235(1): p. 89-97 (1996).

Fahrenberg et al., "A microvalve system fabricated by thermoplastic molding," J. Micromech. Microeng., vol. 5, pp. 169-171(1995).

Ferguson, et al., "A fiber-optic DNA biosensor microarray for the analysis of gene expression," *Nature Biotechnology*, vol. 14, pp. 1681-1684 (1996).

Forster, T., "Delocalized Excitation and Excitation Transfer", Modem Quantum Chem., *Istanbul Lectures*, Part TII, pp. 93-137, Academic Press, New York (1965).

Fritz, I. et al., "Electronic detection of DNA by its intrinsic molecular charge", *PNAS*, vol. 99, No. 22, pp. 14142-14146 (Oct. 2002).

Fu et al., "A microfabricated fluorescence-activated cell sorter," *Nature Biotechnology*, vol. 17, pp. 1109-1111 (1999).

Fu e al., "An integrated microfabricated cell sorter", *Analytical Chemistry*, 74(11): pp. 2451-2457 (2002).

Funatsu, T. et al., "Imaging of single fluorescent molecules and individual ATP turnovers by single myosin molecules in aqueous solution", *Nature*, vol. 374, pp. 555-559 (Apr. 1995).

Garcia, A., "Determination of Ion Penneability by Fluorescence Quenching", *Meth. in Enzymology*, 207:501-511 (1992).

Gardner, A., et al., "Acyclic and dideoxy terminator preferences denote divergent sugar recognition by archaeon and *Taq* DNA polymerases", *Nucleic Acids Research*, vol. 30, No. 2, pp. 605-613 (2002).

Gardner et al., "Comparative kinetics of nucleotide analog incorporation by Vent DNA polymerase," *J. Biol. Chem.*, 279, No. 12, p. 11834-11842 (2004).

Giller et al., "Incorporation of reporter molecule-labeled nucleotides by DNA polymerases. I. Chemical synthesis of various reporter group-labeled 2'deoxyribonucleoside-5'-triphosphates," *Nucleic Acids Res.*, 31, No. 10, p. 2630-2635 (2003).

Giusti, W. et al., "Synthesis and Characterization of 5' —Fluorescent-dye-labeled Oligonucleotides", *PCR Methods and Applications*, 2:223-227 (1993).

Goll et al., "Microvalves with bistable buckled polymer diaphragms,"*J. Micromech. Microeng.*, vol. 6., pp. 77-79 (1996).

Goodwin, P.M., et al., "Application of single molecule detection to DNA sequencing." *Nucleosides & Nucleotides*, 16(5-6): p. 543-550 (1997).

Gravesen et al., "Microfluidics—a review", *J. Micromech. Microeng.*, vol. 3, pp. 168-182 (1993).

Greene, T.W. and P.G.M. Wuts, "Protective Groups in Organic Synthesis." John Wiley & Sons, Inc.: New York, 1999 3rd Ed, pp. xi-xii only (Table of Contents).

Gueroui, Z., et al., "Observation by fluorescence microscopy of transcription on single combed DNA," *PNAS*, 99(9): p. 6005-6010 (2002).

Guilbault, G., "Practical Fluorescence—Theory, Methods and Techniques," Chapters 1 and 3, and pp. 521-524, Marcel Dekker, Inc., New York (1973).

Guillier, F., D. Orain, and M. Bradley, "Linkers and Cleavage Strategies in Solid-Phase Organic Synthesis and Combinatorial Chemistry." Chemical Reviews, 100(6): p. 2091-2157 (2000).

Gupta, K.C., et al., "A general method for the synthesis of 3'-sulfhydryl and phosphate group containing oligonucleotides", *Nucleic Acids Res.*, 1901:3019-25 (1991).

Gyllenstein, U. et al., "Generation of single-stranded DNA by the polymerase chain reaction and its application to direct Sequencing of the *HLA-DQA*locus", *PNAS*, 85:7652-56 (1988).

Ha, "Single molecule dynamics studied by polarization modulation," Phys. Rev. Lett., 77, No. 19, 3979-3982 (1996).

Ha, "Single molecule spectroscopy with automated positioning," Appl. Phys. Lett. 70, No. 6, 782-784 (1997).

Ha, "Single-molecule fluorescence methods for the study of nucleic acids," Current Opinion in Struct Bio, 11, 287-292 (2001).

Ha et al., "Single-molecule fluorescence spectroscopy of enzyme conformational dynamics and cleavage mechanism,"*PNAS*, 96(3): p. 893-898 (1999).

Ha, T., "Single-molecue fluorescence resonance energy transfer," *Methods*, 25(1): p. 78-86 (2001).

Hanna, M. et al., "Synthesis and characterization of a new photocrosslinking CTP analog and its use in photoaffmity labeling *E. coli* and T7 RNA polymerases", *Nucleic Acids Res.*, 21(9):2073-2079 (1993).

Hansen, C.J., et al., "A robust and scalable microfluidic metering method that allows Protein crystal growth by free interface diffusion". Proc Natl Acad Sci U S A, 99 (26): p. 16531-6 (2002).

Harding et al., "Single-molecule detection as an approach to rapid DNA sequencing," Trends in Biotechnology, vol. 10, 3 pages, (1992).

Harris, J.M., "Introduction to Biochemical and biomedical applications of poly(ethylene glycol)." Poly(ethylene glycol) Chemistry, Harris, J. M., Ed.; Plenum Press: New York, pp. 1-14 (1992).

Harrison et al., "Micromachining a miniaturized capillary electrophoresis-based chemical analysis system on a chip," Science, vol. 261, pp. 895-897 (1993).

Harrison, D., et al., "Towards miniaturized electrophoresis and chemical analysis systems on silicon: an alternative to chemical sensors", *Sensors and Actuators B*, 10, pp. 107-116 (1993).

Hasan, A. et al., "Photolabile Protecting Groups for Nucleosides: Synthesis and Photodeprotection Rates", *Tetrahedron*, 53(12):4247-4264 (1997).

Hornbeck, L. et al., "Bistable Defonnable Mirror Device", 1988 Techllical Digest Series, vol. 8, Optical Society of America, pp. 107-110, (Jun. 1988).

Hosokawa et al., "Handling of Picoliter liquid samples in a poly(dimethylsiloxane)-based microfluidic device," Anal. Chem., vol. 71, No. 20, pp. 4781-4785 (1999).

Houseal, T. et al., "Real-time imaging of single DNA molecules with fluorescence microscopy", *Biophys. I.*, vol. 56, pp. 507-516 (Sep. 1989).

Howorka, et al., "Sequence-specific detection of individual DNA strands using engineered nanopores." Nature Biotechnology, 19(7): p. 636-639 (2001).

Hubner et al., "Direct observation of the triplet lifetime quenching of single dye molecules by molecular oxygen," J. Chem. Physics, 115, No. 21, p. 9619-9622 (2001).

Hultman, T. et al., "Bidirectional Solid-Phase Sequencing of In Vitro-Amplified Plasmid DNA", *BioTechniques*, vol. 10, No. 1, pp. 84-93 (1991).

Hyman, E., "A New Method of Sequencing DNA", *Anal. Biochem.*, 174:423-436 (1988).

Ikuta et al., "Three dimensional micro integrated fluid systems (MIFS) fabricated by stereo lithography", *IEEE Kyushu Institute of Technology*, pp. 1-6, (1994).

Ishii et al., "Fluorescence resonance energy transfer between single fluorophores attached to a coiled-coil protein in aqueous solution," Chemical Physics, 247, 163-173 (1999).

Ishijima, A. et al., "Simultaneous Observation of Individual ATPase and Mechanical Events by a Single Myosin Molecule during Interaction with Actin", *Cell*, vol. 92, pp. 161-171, (Jan. 1998).

Ishikawa, M. et al., "Single-Molecule Detection by Laser-Induced Fluorescence Technique with a Position-Sensitive Photon-Counting Apparatus", *Appl. Phys.*, vol. 33, Part 1, No. 3A, pp. 1571-1576 (1994).

Jacobs et al., "Combinatorial chemistry—applications of light-directed chemical synthesis", *TIBTech*, vol. 12, pp. 19-26 (Jan. 1994).

Jacobson, K. et al., "International Workshop on the application of fluorescence photobleaching techniques to problems in cell biology", Workshop Summary, Federation Proceedings, vol. 42, pp. 72-79 (1983).

Jacobson, et al., "High-speed separations on a microchip," Anal. Chem., vol. 66, No. 7, pp. 1114-1118 (1994).

Jacobson, et al., Microfluidic devices for electrokinetically driven parallel and serial mixing, Anal. Chem., vol. 71, No. 20, pp. 4455-4459 (1999).

Jett, J. et al., "High-Speed DNA Sequencing: An Approach Based Upon Fluorescence Detection of Single Molecules", *J. Biomolecular Structure & Dynamics*, vol. 7, No. 2, pp. 301-309, (1989).

Johnston, R. et al., "Autoradiography using storage phosphor technology", *Electrophoresis*, 11:355-360 (1990).

Jongeneel, C.V., et al., "Comprehensive sampling of gene expression in human cell lines with massively parallel signature sequencing". Proc Natl Acad Sci U S A, 100(8), pp. 4702-4705 (2003).

Joos, B. et al., "Covalent Attachment of Hybridizable Oligonucleotides to Glass Supports", *Anal. Biochem*, 247(1):96-101 (1997).

Kambara, H. et al., "Optimization of Parameters in a DNA Sequenator using Fluorescence Detection", *Biotechnology*, vol. 6, pp. 816-821 (1988).

Kartalov, Emil P., et al., "Microfluidic device reads up to four consecutive base pairs in DNA sequencing-by-synthesis", *Nucleic Acids Research*, vol. 32, No. 9, pp. 2873-2879 (2004).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Kartalov et al., "Poly-Electrolyte Surface-Chemistry Platform for Fluorescence Studies of DNA on Glass", http://www.ugcs.caltech.edu/~kartalov/PEM_6.pdf, pp. 1-7, last modified Jun. 7, 2002.

Kawai et al., "A simple method of detecting amplified DNA with immobilized probes on microtiter wells", *Analytical Biochemistry*, 209:63-69 (1993).

Kelso et al., "Single-cell analysis by RT-PCR reveals differential expression of multiple type 1 and 2 cytokine genes among cells within polarized CD4+ T cell populations," International Immunology, 11, No. 4, 617-621 (1999).

Kenis et al., "Microfabrication inside capillaries using multiphase laminar flow patterning," Science, vol. 285, pp. 83-85 (1999).

Kenney, et al., "Mutation Typing Using Electrophoresis and Gel-Immobilized Acrydite™ Probes," BioTechniques, vol. 25, No. 3, pp. 516-521, (1998).

Khandjian, E., "UV cross linking of RNA to nylon membrane enhances hybridization signals", *Mole. Bio, Rep.* 11: 107-115 (1986).

Khrapko, K. et al., "A method for DNA sequencing by hybridization with oligonucleotide matrix", *DNA Sequence-J. DNA Sequencing and Mapping*, vol. 1, pp. 375-388 (1991).

Kiefer, J. et al., "Crystal structure of a thermostable *Bacillus* DNA polymerase I large fragment at 2.1 A resolution", *Structure*, 5:95-108 (1997).

Kim, Y. et al., "Crystal structure of *Thermus aquaticus* DNA polymerase", *Nature*, 376:612-616 (1995).

Kirkland, T.A., D.M. Lynn, and R.H. Grubbs, "Ring-Closing Metathesis in Methanol and Water." Journal of Organic Chemistry, 63(26): p. 9904-9909 (1998).

Knerr, L. and R. R. Schmidt, "Application of a ring-closing-metathesis-based linker to the solid phase synthesis of oligosaccharides" Synlett, 11: p. 1802-1804 (1999).

Kopp, et al., "Chemical Amplification: Continuous-Flow PCR on a Chip", Science, vol. 280, pp. 1046-1048 (May 1998).

Korolev, S. et al., "Crystal structure of the large fragment of *Thermus aquaticus* DNA polymerase I at 2.5 A resolution: Structural basis for thermo stability", *PNAS*, 92:9264-9268 (1995).

Kovacs et al., "Simple synthesis of 5-vinyl-and 5-ethynyl-2' deoxyuridine 5'-triphosphates", Tetrahedron Letters, 29(36): p. 4525-8 (1988).

Kricka et al., "Labels, Labeling, Analytical Strategies, and Applications." Ch. 1 and Table 1x, Academic Press, New York, pp. 3-40, (1995).

Krider, E. et al., "2'-Modified Nucleosides for Site-Specific Labeling of Oligonucleotides", *Bioconjugate Chem.*, vol. 13, No. 1, pp. 155-162 (2002).

Kuhn, L. et al., "Silicon Charge Electrode Array for Ink Jet Printing", *IEEE Trans. On Electron Dev.*, vol. ED-25, No. 10, pp. 1257-1260 (Oct. 1978).

Lacoste, T. et al., "Ultrahigh-resolution multicolor colocalization of single fluorescent probes", *PNAS*, 97(17):9461-6 (2000).

Lander, E.S., et al., "Initial sequencing and analysis of the human genome." Nature, 409(6822): p. 860-921 (2001).

Lazowski, K. et al., "Highly Sensitive Detection of Hybridization of Oligonucleotides to Specific Sequences of Nucleic Acids by Application of Fluorescence Resonance Energy Transfer", *Antisense and Nucleic Acid Drug Dev.*, vol. 10, pp. 97-103 (2000).

Lee, "Enhancing the catalytic repertoire of nucleic acids: a systematic study of linker length and rigidity," Nucleic Acids Res., 29, No. 7, Apr. 1, 1565-1573 (2001).

Lee, Y. et al., "Laser-Induced Fluorescence Detection of a Single Molecule in a Capillary", *Anal. Chem.*, vol. 66, pp. 4142-4149 (1994).

Levene, M. et al., "Zero-Mode Waveguides for Single-Molecule Analysis at High Concentrations", *Science*, 299:682-686 (Jan. 2003).

Levsky et al., "Single-cell gene expression profiling," Science, 297, 836-840 (2002).

Li, H. et al., "Ultrasensitive Coincidence Fluorescence Detection of Single DNA Molecules", *Anal. Chem.*, 75:1664-1670 (2003).

Li, Y. et al., "Design, Synthesis, and Spectroscopic Properties of Peptide-Bridged Fluorescence Energy-Transfer Cassettes", *Bioconjuate Chem.*, 10:241-245 (1999).

Li, Y. et al., "Structural Studies of the Klentaq1 DNA Polymerase", *Current Organic Chem.*, 5:871-883 (2001).

Li, Z. et al., "A photocleavable fluorescent nucleotide for DNA sequencing and analysis", *PNAS*, vol. 100, No. 2, pp. 414-419 (2003).

Lin, L. et al., "Free-Space Micromachined Optical Switches for Optical Networking", *IEEE J. of Selected Topics in Quanturn Electronics*, vol. 5, No. 1, pp. 4-9 (Jan. 1999).

Liu, J., M.. Enzelberger, and S. Quake, "A nanoliter rotary device for polymerase chain reaction" Electrophoresis, 23(10): p. 1531-6 (2002).

Lodder, M., et al., "Misacylated Transfer RNAs Having a Chemically Removable Protecting Group." Journal of Organic Chemistry, 63(3): p. 794-803 (1998).

Loh, E. et al., "Polymerase Chain Reaction with Single-Sided Specificity: Analysis of T Cell Receptor D Chain", *Science* 243:217-220 (1989).

Lok, Corie, "Deciphering DNA, Top Speed—Helicos BioSciences aims to expedite sequencing, enable genomic medicine," *Technology Review*, pp. 27-28 (May 2005).

Lopez, G. et al., "Fabrication and Imaging of Two-Dimensional Patterns of Proteins Adsorbed on Self-Assembled Monolayers by Scanning Electron Microscopy", *J. Arner. Chem. Soc.*, 115:10774-81 (1993).

Lotters et al., "The mechanical properties of the rubber elastic polymer polydimethylsiloxane for sensor applications," J. Micromech. Microeng., vol. 7, pp. 145-147 (1997).

Lucy et al., "Characterization of the cationic surfactant induced reversal of electroosmotic flow in capillary electrophoresis," Anal. Chem., vol. 68, pp. 300-305 (1996).

Ludwig, J and F. Eckstein, "Rapid and Efficient Synthesis of Nucleoside 5'-0-(1-Thiotriphosphates), 5'- triphosphates and 2',3'-Cyclophosphorothioates Using 2-Chloro-4$H$-1,3,2-benzodioxaphosphorin- 4-one." Journal of Organic Chemistry, 54(3): p. 631-635 (1989).

Lvov, Yu. et al., "Assembly of Thin Films by Means of Successive Deposition of Alternate Layers of DNA and Poly(allylamine)", *American Chemical Society, Macromolecules*, 26, pp. 5396-5399, (1993).

Macklin, J. et al., "Imaging and Time-Resolved Spectroscopy of Single Molecules at an Interface", *Science*, vol. 272, No. 5259, pp. 255-258 (Apr. 1996).

Maier, B., D. Bensimon, and V. Croquette, "Replication by a single DNA polymerase of a stretched single-stranded DNA." Proceedings of the National Academy of Sciences of the United States of America, 97(22): p. 12002-12007 (2000).

Marriott, G. et al., "Time resolved imaging microscopy—Phosphorescence and delayed fluorescence imaging", *Biophys. J.*, vol. 60, pp. 1374-1387 (Dec. 1991).

Marziali, A. and M. Akeson, "New DNA sequencing methods." Annual Review of Biomedical Engineering, 3: p. 195-223 (2001).

Mastrangelo, C. et al., "Vacuum-Sealed Silicon Micromachined Incandescent Light Source", *IDEM*, 89:503-506 (1989).

Meiners, J.C and S.R. Quake, "Femonewton force spectroscopy of single extended DNA molecules." Phys Rev Lett, 84(21): p. 5014-7 (2000).

Meldrum, Kevin, "Microfluidics-based products for nucleic acid analysis", http://www.americanlaboratory.com/articles/al/a9909mel.pdf, 2 pages (Sep. 1999).

Meller, A., et al., "Rapid nanopore discrimination between single polynucleotide molecules." *PNAS*, 97(3): p. 1079-1084 (2000).

Mertz, J. et al., "Single-molecule detection by two-photon-excited fluorescence", *Optics Letters*, vol. 20, No. 24, pp. 2532-2534 (Dec. 1995).

Metzker et al., "Elimination of residual natural nucleotides from 3'-O-modified-dNTP syntheses by enzymatic mop-up," BioTechniques, 25, 814-817 (1998).

Metzker, M.L., et al., "Termination of DNA synthesis by novel 3'-modified-deoxyribonucleoside 5'- triphosphates." Nucleic Acids Res, 22(20): p. 4259-67 (1994).

Mitra, Robi, et al., "Fluorescent in situ sequencing on polymerase colonies", *Analytical Biochemistry*, 320, pp. 55-65 (2003).

Moe et al., Rapid Detection of Clinically Relevant Bacteria in Platelets Using the Hybriscan Baceterial Detection system, Journal of the American Society of Hematology, 96, No. 11, 4155 (2000).

Moore, P., "To affinity and beyond", *Nature*, vol. 426, No. 6967, pp. 725-731, (2003).

Muller et al., "Surface-micromachined microoptical elements and systems," IEEE vol. 86, No. 8, pp. 1705-1720 (1998).

Nelson, P. et al., "Bifunctional oligonucleotide probes synthesized using a novel CPG support are able to detect single base pair mutations", *NAR*, 17(18):7187-7194 (1989).

Nie, S. et al., "Probing Individual Molecules with Confocal Fluorescence Microscopy", *Science*, vol. 266, No. 5187, pp. 1018-1021 (Nov. 1994).

Nyren, P. et al., "Solid Phase DNA Minisequencing by an Enzymatic Luminometric Inorganic Pyrophosphate Detection Assay", *Anal. Biochem.*, vol. 208, pp. 171-175 (1993).

Ochman, H. et al., "Genetic Applications of an Inverse Polymerase Chain Reaction", *Genetics* 120:621-623 (1988).

Ohara, To et at, "'Wired' Enzyme Electrodes for Amperometric Determination of Glucose or Lactate in the Presence of Interfering Substances",Anal. *Chem.*, vol. 66, No. 15, pp. 2451-2457 (Aug. 1994).

Ohara, T. et al., "Glucose Electrodes Based on Cross-Linked [Os(bpY)2CltH Complexed Poly(1-vinylimidazole) Films", *Anal. Chem.*, vol. 65, pp. 3512-3517 (1993).

Okabe, S. et al., "Do Photobleached Fluorescent Microtubules Move?: Re-evaluation of Fluorescence Laser Photobleaching both In Vitro and in Growing Xenopus Axon", *J. Cell Bio.*, vol. 120, No. 5, pp. 1177-1186 (1993).

Ollis, D. et al., Structure of large fragment of *E. coli* DNA polymerase I complexed with Dtmp, *Nature*, 313:762-766 (1985).

Oroskar, A. et al., "Detection of immobilized amplicons by ELISA-like techniques" *Clin. Chem.*, 42(9):1547-1555 (1996).

Patchornik, A. et al., "Photosensitive Protecting Groups" *J. Arner. Chem. Soc.*, 92(21):6333-37 (1970).

Padmaja, T., et al., "Enzymatically degradable prodrugs: a novel methodology for drug linkage." Journal of Applied Polymer Science, 85(10): p. 2108-2118 (2002).

Pennisi, E., "Gene researchers hunt bargins, fixer-uppers." Science, 298(5594): p. 735-736 (2002).

Perales et al., "Enhancement of DNA, cDNA synthesis and fidelity at high temperatures by a dimeric single-stranded DNA-binding protein," Nucleic Acids Res., 31, No. 22, 6473-6480 (2003).

Perkins, T. et al., "Relaxation of a Single DNA Molecule Observed by Optical Microscopy", *Science*, 264:822-826 (May 1994).

Pethig, R. et at, "Applications of dielectrophoresis in biotechnology", *Tibtech*, vol. 15, pp. 426-432 (Oct. 1997).

Pisani, F. et at, "Domain Organization and DNA-Induced Conformational Changes of an Archaeal Family B DNA Polymerase", *Biochemistry*, vol. 35, pp. 9158-9166 (Jul. 1996).

Plakhotnik, T. et at, "Single-Molecule Spectroscopy", *Annu, Rev. Phys. Chem.*, vol. 48, pp. 181-212 (1997).

Ploem, J., Ch. 1 "Fluorescence Microscopy", Fluorescent and Luminescent Probes for Biological Activity, Mason, T. Ed., Academic Press, London, pp. 1-11 (1993).

Qin et al., "Elastomeric Light Valves," *Advanced Materials*, vol. 9, No. 5, pp. 407-410 (1997).

Qin, P. et al., "Site-Specific Labeling of RNA with Fluorophores and Other Structural Probes", *Methods*, vol. 18, No. 1, pp. 60-70 (May 1999).

Quake, S. et al., "Fluorescent Photobleaching Method for Sequencing DNA", pp. 1-10, circa 1996.

Quake, Stephen R. et al., "Methods and Apparatuses For Analyzing Polynucleotide Sequences", pending U.S. patent application, U.S. Appl. No. 09/707,737, filed Nov. 6, 2000.

Quake, S. et al., "Polymer Physics with Single Molecules of DNA" (Dept. of Physics), a colloquium by Stephen Quake, Stanford University, Feb. 22, 1996. (Presented at Laser Spectroscopy XII Intl. Conference, Italy, Jun. 1995.).

Quake, S. et al., "From Micro- to Nanofabrication with Soft Materials", *Science*, vol. 290, No. 5496, pp. 1536-1540 (Nov. 2000).

Rapp, R. et al., "L1GA micropump for gases and liquids", *Sensors and Actuators A*, vol. 40, pp. 57-61 (1994).

Rasolonjatovo I. and S.R. Sarfati, "6-N-(N-methylanthranyamido)-4-oxo-hexanoic acid: a new florescent protecting group applicable to a new DNA sequencing method." Nucleosides & Nucleotides, 17(9-11): p. 2021-2025 (1998).

Rasolonjatovo, I. and Sarfati, "Development of a new DNA sequencing method: 3'-ester cleavage catalyzed by Taq DNA polymerase." Nucleosides & Nucleotides, 18(4 & 5): p. 1021-1022 (1999).

Reha-Krantz, L. et al., "Genetic and Biochemical Studies of Bacteriophage T4 DNA Polymerase 3'→5'- Exonuclease Activity", *The Journal of Biological Chemistry*, vol. 268, No. 36, pp. 27100-27108 (1993).

Reha-Krantz, L. et al., "Motif A of Bacteriophage T4 DNA Polymerase: Role in Primer Extension and DNA Replication Fidelity", *The Journal of Biological Chemistry*, vol. 269, No. 8, pp. 5635-5643 (1994).

Rigler, R, et al, "DNA-sequencing at the single molecule level." Journal of Biotechnology, 86(3): p. 161 (2001).

Rigler, R., "Fluorescence correlations, single molecule detection and large number screening—Applications in Biotechnology", *J. Biotech.*, 41: 177-186 (1995).

Ronaghi, M. et al., "A Sequencing Method Based on Real-Time Pyrophosphate", *Science*, vol. 281, pp. 363-365 (Jul. 1998).

Ronaghi, M et al., "Real-Time DNA Sequencing Using Detection of Pyrophosphate Release." *Analytical BioChemistry*, 242, No. 0432, (1996), pp. 84-89.

Rosenblum, B. et al., "New dye-labeled terminators for improved DNA sequencing patterns ",*Nucleic Acids Research*, vol. 25, No. 22, pp. 4500-4504 (Nov. 1997).

Rosenblum, B. et al., "Improved single-strand DNA sizing accuracy in capillary electrophoresis", *Nucleic Acids Research*, vol. 25, No. 19, pp. 3925-3929 (Oct. 1997).

Roylance, L. et al., "A Batch-Fabricated Silicon Accelerometer", *IEEE Trans. On Elec. Dev.*, vol. ED-26, No. 12, pp. 1911-1917(1979).

Ruparel, Hameer, "Design and synthesis of a 3'-O-allyl photocleavable fluorescent nucleotide as a reversible terminator for DNA sequencing by synthesis", *PNAS*, vol. 102, No. 17, pp. 5932-5937 (Apr. 26, 2005).

Ruth, J. et al., "Nucleoside Analogues with Clinical Potential in Antivirus Chemotherapy", *Molecular Pharmacology*, 20:415-422 (1981).

Sanger, F. et al., "DNA sequencing with chain-terminating inhibitors", *PNAS*, 74(12):5463-67 (Dec. 1977).

Sarfati, S.R., et al., "Synthesis of fluorescent derivatives of 3'-O-(6-aminohexanoyl)-pyrimidine nucleosides 5'- triphosphates that act as DNA polymerase substrates reversibly tagged at C-3'." Journal of the Chemical Society, Perkin Transactions I: Organic and Bio-Organic Chemistry, 9: p. 1163-1171 (1995).

Sato, E. et al., "Bimane Conjugates of 5-Halogenouridylic Acids as Fluorogenic Substrates for Phosphodiesterase I", *J. Chem. Research (S)*, Issue 10, pp. 390-391 (1994).

Satoh, Ikuo et al., "Flow-injection determination of inorganic pyrophosphate with use of an enzyme thermistor containing immobilized inorganic pyrophosphatase", *Chemical Abstracts*, vol. 110, No. 16, pp. 409-413 (1988).

Sauer, M., et al.., "Single molecule DNA sequencing in submicrometer channels: state of the art and future prospects." Journal of Biotechnology, 86(3): p. 181-201 (2001).

Schasfoort et al., "Field-effect flow control for microfabricated fluidic networks," Science, vol. 286, pp. 942-945 (1999).

Schueller, O., et al., "Reconfigurable diffraction gratings based on elastomeric microfluidic devices", *Sensors and Actuators*, 78, pp. 149-159 (1998).

Seeger, S. et al., "Single molecule fluorescence—High Performance Molecular Diagnosis and Screening", translated from *BIOforum*, pp. 179-185, (Apr. 1998).

Selvin, P., "Fluorescence Resonance Energy Transfer", *Meth. In Enzymology*, vol. 246, pp. 300-335, Academic Press (1995).

Seo, Tae Seok, "Four-color DNA sequencing by synthesis on a chip using photocleavable fluorescent nucleotides", *PNAS*, vol. 102, No. 17, pp. 5926-5931 (Apr. 26, 2005).

Seo, Tae Seok, "Photocleavable fluorescent nucleotides for DNA sequencing on a chip constructed by site-specific coupling chemistry", *PNAs*, vol. 101, No. 15, pp. 5488-5493 (Apr. 13, 2004).

Shackelford, James F., "Intro. to Materials Science for Engineers," $3^{rd}$ Edition, Prentice-Hall, Inc., Macmillan Publ. Co. (1992), pp. xiii-xviii table of contents.

Shendure et al., "Advanced sequencing technologies: Methods and goals," *Nature Reviews*, vol. 5, No. 5, pp. 335-344 (2004).

Shoji, S. et al., "Smallest Dead volume Microvalves for Integrated Chemical Analyzing Systems", *Proceedings of Transducers '91*, IEEE, pp. 1052-1055, San Francisco (1991).

Shoji, S. et al., "Fluids for Sensor Systems." Microsystem Technology in Chemistry and Life Science, Topics in Current Chem., vol. 194, pp. 162-188, Springer-Verlag (1998).

Smith, L. et al., "Fluorescence detection in automated DNA sequence analysis", *Nature*, vol. 321, pp. 674-679 (Jun. 1986).

Smith, L. et al., "The synthesis of oligonucleotides containing an aliphatic amino group at the 5' terminus: synthesis of fluorescent DNA primers for use in DNA sequence analysis", *Nucleic Acids Res.*, vol. 13, No. 7, pp. 2399-2412 (1985).

Smith, S. et al., "Direct Mechanical Measurements of the Elasticity of Single DNA Molecules by Using Magnetic Beads", *Science* 258:1122-26 (1992).

Smits, 1., "Piezoelectric Micropump with Three Valves Working Peristaltically", *Sensors and Actuators*, vol. A21-A23, pp. 203-206 (1990).

Song et al., "Influence of the triplet excited state on the photobleaching kinetics of fluorescein in microscopy," Biophysics J., 70, 2959-2968 (1996).

Sproat, B. et al., "The synthesis of protected 5'-mercapto-2',5'-dideoxyribonucleoside- 3' O-phosphoramidities; uses of 5' -mercapto-oligodeosyribonucleotides", *Nucleic Acids Res.*, 15(12):4837-48 (1987).

Stocki, S. et al., "Dynamics of Bacteriophage T4 DNA Polymerase Function: Identification of Amino Acid Residues that Affect Switching between Polymerase and 3'→5'-Exonuclease Activities", *J. Mol. Biol.*, 254, pp. 15-28 (1995).

Strausberg, R L, et al., "The mammalian gene collection." Science, 286(5439): p. 455-7 (1999).

Sukhorukov, G.B., et al., "Assembly of polyelectrolyte multilayer films by consecutively alternating adsorption of polynucleotides and polycations", *Thin Solid Films*, 284-285, pp. 220-223 (1996).

Tasara et al., "Incorporation of reporter molecule-labeled nucleotides by DNA polymerases. II. High-density labeling of natural DNA," Nucleic Acids Res., 31, No. 10, 2636-2646 (2003).

Taveira, N. et al., "Detection of HI VI proviral DNA by PCR and hybridization with digoxigenin labeled probes", *Mol. Cell Probes*, vol. 6, No. 4, pp. 265-270 (1992).

Taylor, D. et al., "Characterization of chemisorbed monolayers by surface potential measurements", J. *Phys. D. Appl. Phys.* 24:1443-50 (1991).

Terry, S. et al., "A Gas Chromatographic Air Analyzer Fabricated on a Silicon Wafer", *IEEE Trans. on Electron Dev.*, vol. Ed-26, No. 12, pp. 1880-1886 (1979).

Theisen, P. et al., "Fluorescent dye phosphoramidite labeling of oligonucleotides", *Nucleic Acids Symp. Ser.*, vol. 27, pp. 99-100 (1992).

Thompson, N. et al., "Measuring Surface Dynamics of Biomolecules by Total Internal Reflection Fluorescence with Photobleaching Recovery or Correlation Spectroscopy", *Biophys. J.*, vol. 33, pp. 435-454 (Mar. 1981).

Thompson, N. et al., "Immunoglobulin Surface-Binding Kinetics Studied by Total Internal Reflection with Fluorescence Correlation Spectroscopy", *Biophys. J.*, vol. 43, pp. 103-114 (Jul. 1983).

Thorsen, T. S.J. Maerkl, and S.R. Quake, "Microfluidic large-scale integration." Science 298( 5593): p. 580-4 (2002).

Tokunaga, M. et al., "Single Molecule Imaging of Fluorophores and Enzymatic Reactions Achieved by Objective-Type Total Internal Reflection Fluorescence Microscopy", *Biochem. And Biophys. Res. Comm.*, vol. 235, pp. 47-53 (1997).

Toneguzzo, F. et al., "Use of a Chemically Modified T7 DNA Polymerase for Manual and Automated Sequencing of Super coiled DNA", *BioTech*, vol. 6, No. 5, pp. 460-469 (1988).

Trager, R. S., "DNA sequencing—Venter's next goal: 1000 human genomes." Science, 298(5595): p. 947 (2002).

Tufte, O. et al., "Silicon Diffused-Element Piezoresistive Diaphragms", *J. Applied Phys.*, vol. 31, No. 11, pp. 3322- 3327 (Nov. 1962).

Tyagi, S. et al., "Multicolor molecular beacons for allele discrimination", *Nat. Biotechnol.*, 16:49-53 (1998).

Ullman's Encyclopedia of industrial Chemistry, 6ID Edition, vol. 6, Sections 6 to 6.3, Subject: Carbon Black, Wiley-VCH (1999), pp. 350-354.

Unger et al., "Monolithic microfabricated valves and pumps by multilayer soft lithography," Science 288: 113-116 (2000).

Unger, M. et al., "Single-Molecule Fluorescence Observed with Mercury Lamp Illumination", *BioTechniques*, vol. 27, PD. 1008-1014 (Nov. 1999).

Vale, R. et al., "Direct observation of single kinesin molecules moving along microtubules", *Nature*, vol. 380, pp. 451-453, (Apr. 1996).

Van Dam, R.M. and S.R Quake, "Gene expression analysis with universal n-mer arrays." Genome Res, 12(1): p. 145-52 (2002).

Van De Pol, F. et al., "Micro-liquid handling devices: A Review", Micro System Technologies 90, $1^{st}$ Intl. Conf. On Micro Electro, Opto, Mechanic Systems and Components, pp. 799-805, Berlin, Springer-Verlag, (1990).

Van Oijen et al., "Single molecule kinetics of λ exonuclease reveal base dependence and dynamic disorder," Science, 301, 1235-1238 (2003).

Venter, J.L., et al., "The sequence of the human genome." Science, 291(5507): p. 1304-1351 (2001).

Vieider, C. et al., "A Pneumatically Actuated Micro Valve With A Silicone Rubber Membrane For Integration With Fluid-Handling Systems", *Proceedings of Transducers '95*, pp. 284-286, Stockholm (1995).

Walker, M.G., et al., "Prediction of gene function by genome-scale expression analysis: Prostate cancer-associated genes.": Genome Researce, 9(12): p. 1198-1203 (1999).

Wang, G. et al., "Design and Synthesis of New Fluorogenic HIV Protease Substrates Based on Resonance Energy Transfer", *Tetrahedron Lett.*, 31(45):6493-96 (1990).

Wang, M.D., et al," Force and Velocity measured for single molecules of RNA polymerase." Science, 282(5390): p. 902-907 (1998).

Washizu et al., "Molecular dielectrophoresis of biopolymers," IEEE Transactions on Industry Applications, vol. 30, No. 4, pp. 835-843 (1994).

Watkins, R. et al., "A Total Internal-Reflection Technique for the Examination of Protein Adsorption", *J. Biomed. Mater. Res.*, vol. 11, pp. 915-938 (1977).

Weber, J.L. and E.W. Myers, "Human whole-genome shotgun sequencing." Genome Research, 7(5): p. 401-409 (1997).

Webster, J. et al., "Monolithic Capillary Gel Electrophoresis Stage with On-Chip Detector", Intl. Conf on MEMS (MEMS 96), pp. 491-496 (1996).

Wedekind, P. et al., "Scanning microphotolysis: a new photobleaching technique based on fast intensity modulation of a scanned laser beam and confocal imaging", *J. Microscopy*, vol. 176, Pt. 1 , pp. 23-33 (Oct. 1994).

Weir, et al., "Hybrigel Purification: A Novel Technique for Accelerated Prepration of DNA Sequence Products for Capillary Electrophoresis and Multiplexing," Clinical Chemistry, vol. 45, No. 11, p. 2052 (1999).

Weiss, S., "Fluorescence Spectroscopy of Single Biomolecules", *Science*, vol. 283, pp. 1676-1683 (Mar. 1999).

Welch, M.B. and K. Burgess, "Synthesis of fluorescent, photolabile 3'-0-protected nucleoside triphosphates for the base addition sequencing scheme." Nucleosides & Nucleotides, 18(2): p. 197-201 (1999).

Werner et al "Progress towards single-molecule DNA sequencing: a one color demonstration." J Biotechnol, 102(1): p. 1-14 (2003).

Williams, N. et al., "Exploring the Adenine Nucleotide Binding Sites on Mitochondrial $F_1$-ATPase with a New Photoaffinity Probe, 3'-O-(4-Benzoyl)benzoyl Adenosine 5'-Triphosphate", *J. Bioi. Chem.*, 237(6):2834-41 (1982).

Winter et al., "Direct gene expression analysis," Curr. Pharm. Biotech., 5, p. 191-197 (2004).

Wu, et al., "Synthesis and Properties of Adenosine-5'-triphosphoro-γ-l-(5-sulfonic acid)naphthyl Ethylamide: A Fluorescent Nucleotide Substrate for DNA-Dependent RNA Polymerase from *Escherichia coli*," Archives of Biochemistry and Biophysics, vol. 246, No. 2, pp. 564-571 (1986).

Wuite, G. et al., "Single-molecule studies of the effect of template tension on T7 DNA polymerase activity", *Nature*, 404:103-6 (2000).

Xia et al., "Complex optical surfaces formed by replica molding against elastomeric masters," Science vol. 273, pp. 347-349 (1996).

Xia et al. "Soft Lithography," Angew. Chem. Int. Ed. vol. 37, pp. 551-575 (1998).

Xia, G., et al., "Directed evolution of novel polymerase activities: mutation of a DNA polymerase into a efficient RNA polymerase." Proc Natl Acad Sci USA; 99(10) p. 6597-6602 (2002).

Xie, "Single molecule approach to dispersed kinetics and dynamic disorder: Probing conformational fluctuation and enzymatic dynamics," J. Chem. Physics, 117, No. 24, p. 11024-11032 (2002).

Xu, X. et al., "Direct Measurement of Single-Molecule Diffusion and Photodecomposition in Free Solution", *Science*, vol. 275, pp. 1106-1109, (Feb. 1997).

Xu, X. et al., "Long-Range Electrostatic Trapping of Single-Protein Molecules at a Liquid-Solid Interface", *Science*, vol. 281, pp. 1650-1653 (Sep. 1998).

Yang et al., "A Mems Thermopneumatic Silicone Rubber Membrane Valve", Proceedings of IEEE 10th Annual International Workshop on MicroElectro Mechanical Systems, Sensors and Actuators, vol. A64, No. 1, pp. 101-108 (1998).

Yazdi, N. et al., "Micromachined Inertial Sensors", *Proceedings of the IEEE*, vol. 86, No., pp. 1640-1659 (Aug. 1998).

Yershov, G. et al., "DNA analysis and diagnostics on oligonucleotide microchips", *Proc. Natl. Acad. Sci. USA*, vol. 93, pp. 4913-4918 (May 1996).

Young et al., "Contoured elastic-membrane microvalves for microfluidic network integration," J. Biomechanical Engineering, vol. 121, pp. 2-6 (1999).

Yu., et al., "Cyanine dye dUTP analogs for enzymatic labeling of DNA probes." Nucleic Acids Res, 22(15): p, 3226-32 (1994).

Zdeblick, M. et al., "A Microminiature Electric-To-Fluidic Valve", Transducers '87, reprinted in *Micromechanics and MEMS Classic and Seminal Papers to 1990*, IEEE Press, pp. 437-439 (1987).

Zhu, Z. et al., "Molecular Mechanism Controlling the Incorporation of Fluorescent Nucleotides into DNA by PCR", *Cytometry*, 28:206-211 (1997).

Zhu, Z. et al., "Directly labeled DNA probes using fluorescent nucleotides with different length linkers", *Nucleic Acids Res.*, vol. 22, No. 16, pp. 3418-3422 (1994).

Zuckerman, R. et al., "Efficient methods for attachment of thiol specific probes to the 3' ends of synthetic oligodeoxyribonucleotides", *Nucleic Acids Res.*, 15(13):5305-5321 (1987).

Therminator DNA Polymerase FAQ, http://www.neb.com/nebecomm/products/faqproductM0261.asp downloaded Jun. 1, 2005, 1 page.

The International Search Report and The Written Opinion Of The International Searching Authority from corresponding PCT application No. PCT/US2005/018602, dated Sep. 27, 2006 (13 pages).

* cited by examiner

SEQUENCE LISTING

<160> NUMBER OF SEQ ID NOS: 4

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 1

-continued

```
gggggggtt tttttt                                                      16

<210> SEQ ID NO 2
<211> LENGTH: 16
<212> TYPE: DNA
<213> ORGANISM: Homo sapiens

<400> SEQUENCE: 2
aaaaaaaccc cccccc                                                     16

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggggggtt tttttttttt ttcgtcct                                        28

<210> SEQ ID NO 4
<211> LENGTH: 28
<212> TYPE: DNA
<213> ORGANISM: Homo sapiens

<400> SEQUENCE: 4
tacggacgaa aaaaaaaaac cccccccc                                        28
```

METHODS AND DEVICES FOR NUCLEIC ACID SEQUENCE DETERMINATION

REFERENCE TO RELATED APPLICATIONS

This non-provisional patent application claims the benefit of and priority to U.S. provisional application No. 60/574,389, filed May 25, 2004, the entirety of which is hereby incorporated by reference.

TECHNICAL FIELD OF THE INVENTION

The invention relates to methods and devices for sequencing a nucleic acid, and more particularly, to methods and devices for preparing a surface for high throughput single molecule sequencing of target nucleic acids. Surfaces according to the invention are treated to minimize non-specific binding of molecules.

BACKGROUND OF THE INVENTION

Completion of the human genome has paved the way for important insights into biologic structure and function. Knowledge of the human genome has given rise to inquiry into individual differences, as well as differences within an individual, as the basis for differences in biological function and dysfunction. For example, single nucleotide differences between individuals, called single nucleotide polymorphisms (SNPs), are responsible for dramatic phenotypic differences. Those differences can be outward expressions of phenotype or can involve the likelihood that an individual will get a specific disease or how that individual will respond to treatment. Moreover, subtle genomic changes have been shown to be responsible for the manifestation of genetic diseases, such as cancer. A true understanding of the complexities in either normal or abnormal function will require large amounts of specific sequence information.

An understanding of cancer also requires an understanding of genomic sequence complexity. Cancer is a disease that is rooted in heterogeneous genomic instability. Most cancers develop from a series of genomic changes, some subtle and some significant, that occur in a small subpopulation of cells. Knowledge of the sequence variations that lead to cancer will lead to an understanding of the etiology of the disease, as well as ways to treat and prevent it. An essential first step in understanding genomic complexity is the ability to perform high-resolution sequencing.

Various approaches to nucleic acid sequencing exist. One conventional way to do bulk sequencing is by chain termination and gel separation, essentially as described by Sanger et al., Proc. Natl. Acad. Sci., 74(12): 5463-67 (1977). That method relies on the generation of a mixed population of nucleic acid fragments representing terminations at each base in a sequence. The fragments are then run on an electrophoretic gel and the sequence is revealed by the order of fragments in the gel. Another conventional bulk sequencing method relies on chemical degradation of nucleic acid fragments. See, Maxam et al., Proc. Natl. Acad. Sci., 74: 560-564 (1977). Finally, methods have been developed based upon sequencing by hybridization. See, e.g., Drmanac, et al., Nature Biotech., 16: 54-58 (1998).

Conventional nucleotide sequencing is accomplished through bulk techniques. However, bulk sequencing techniques are not useful for the identification of subtle or rare nucleotide changes due to the many cloning, amplification and electrophoresis steps that complicate the process of gaining useful information regarding individual nucleotides. As such, research has evolved toward methods for rapid sequencing, such as single molecule sequencing technologies. The ability to sequence and gain information from single molecules obtained from an individual patient is the next milestone for genomic sequencing. However, effective diagnosis and management of important diseases through single molecule sequencing is impeded by lack of cost-effective tools and methods for screening individual molecules.

There have been many proposals to develop new sequencing technologies based on single-molecule measurements, generally either by observing the interaction of particular proteins with DNA or by using ultra high resolution scanned probe microscopy. See, e.g., Rigler, et al., *DNA-Sequencing at the Single Molecule Level*, Journal of Biotechnology, 86(3): 161 (2001); Goodwin, P. M., et al., *Application of Single Molecule Detection to DNA Sequencing*. Nucleosides & Nucleotides, 16(5-6): 543-550 (1997); Howorka, S., et al., *Sequence-Specific Detection of Individual DNA Strands using Engineered Nanopores*, Nature Biotechnology, 19(7): 636-639 (2001); Meller, A., et al., *Rapid Nanopore Discrimination Between Single Polynucleotide Molecules*, Proceedings of the National Academy of Sciences of the United States of America, 97(3): 1079-1084 (2000); Driscoll, R. J., et al., *Atomic-Scale Imaging of DNA Using Scanning Tunneling Microscopy*. Nature, 346(6281): 294-296 (1990). Unlike conventional sequencing technologies, their speed and read-length would not be inherently limited by the resolving power of electrophoretic separation. Other methods proposed for single molecule sequencing include detecting individual nucleotides incorporated sequencing by synthesis.

In theory, single molecule techniques on substrates certainly have several advantages over bulk techniques, but implementation has been problematic due to high background signal resulting from inadequate surfaces that fail to enable discriminating signal detection in the single molecule context. Surfaces suitable for nucleic acid detection are a significant issue in sequencing generally and single molecule sequencing in particular. A primary difficulty with most conventional surfaces is that they are susceptible to significant background radiation. For example, when fluorescent detection is used in sequencing, the background radiation problem becomes even more acute.

Accordingly, there is a need in the art for methods and devices for sequencing generally and single molecule sequencing in particular including surfaces of substrates appropriate for nucleic acid detection.

SUMMARY OF THE INVENTION

The invention provides surfaces for the detection of attached molecules and methods for molecular detection using surface chemistries of the invention. According to the invention, enhanced molecular signal detection is achieved on a solid support by treating the support to simultaneously reduce background and enhance signal. The invention provides surface preparation strategies, molecule attachment strategies, and washing strategies that result in improved signal detection on a surface.

The invention provides surfaces that feature improved molecular attachment, improved surface blocking to prevent non-specific attachment, and improved rinsing strategies to remove non-specifically bound molecules. The result is a surface to which desired substrate molecules adhere and that features minimized noise due to non-specific surface residue.

Strategies for attachment, blocking, and rinsing are tailored to the molecule to be attached and the chemistry to be performed on the surface. However, in general, the invention provides strategies that minimize non-specific surface interactions and favor specified reactive molecules. For example, if non-specific binding is driven by hydrophobic interactions, the surface is treated with a non-reactive hydrophobic reagent to break up the non-specific surface interaction between the adherent species. Other active rinsing strategies are provided below. General surface blocking techniques also use non-reactive species to out-compete non-specific binding that might interfere with detection. Finally, attachment strategies include molecule-specific chemistries between the reactive species and a surface layer. Various alternatives are presented below.

A preferred method of the invention comprises attaching a molecule of interest to a surface under conditions that promote stable attachment and wash-resistance, blocking the surface to diminish or prevent background, conducting a chemical reaction involving the molecules of interest, and rinsing the surface to remove unreacted or undesired molecules such that the molecules of interest remain intact. In some embodiments, rinsing comprises active rinsing and passive rinsing, active rinsing being with an agent that actively removes unwanted surface contamination.

Preferred surfaces of the invention include epoxide and epoxide derivative surfaces. In one preferred embodiment, a streptavidinated epoxide surface is used as described below. Other preferred surfaces include aldehydes and activated amino surfaces. The choice of a surface will depend upon the chemistry to be conducted on it and is within the ordinary skill in the art in light of the guidance provided herein. Any surface for use in the invention may be functionalized in order to promote optimal surface chemistry. Several such functionalized surfaces are presented herein.

Attachment of reactive species (e.g., proteins, nucleic acids, etc.) is by either direct or indirect means. On an epoxide surface, attachment is either via direct attachment through a reactive amino addition or indirect attachment via a bi-functional bridge. A preferred means of indirect attachment is via a biotin-streptavidin linkage, especially when the reactive molecule is a nucleic acid.

Preferred blocking strategies include exposing the surface to a non-detectable molecule that adheres to the surface or changes the chemical properties of the surface such that non-specific binding are reduced. In methods in which optically-detectable labels are used, one way to block or passivate the surface is to expose the surface to unlabeled molecules of the same type as those that are labeled. In that situation, the unlabeled molecules will outcompete labeled molecules for non-specific binding on the surface, thus reducing background due to non-specific label. Other strategies involve treating the surface with phosphate, Tris, a sulfate, or an amine that interacts with the surface to prevent non-specific binding. Non-reactive proteins are also appropriate. In a preferred embodiment, a matrix of blocking reagents is provided on the surface in order to provide a highly washable, low non-specific background surface. In some embodiments, blocking reagents are chosen to provide electrostatic repulsion of highly anionic nucleoside triphosphates.

Preferred rinsing strategies engage wash components that displace non-reactive or non-specifically adherent material, but do not destabilize reactive species on the surface. In one embodiment, an epoxide surface is rinsed with acetonitrile in order to displace unreactive components. In a preferred embodiment, a solution of between about 10% and about 50%, preferably 30% acetonitrile is used. Whether or not an active rinse agent is used, passive rinsing may also be employed with, for example, water or buffer.

In a preferred embodiment of the invention, nucleic acids are attached to surfaces that are prepared to minimize background for optical detection of incorporated nucleotides in a template-dependent synthesis reaction conducted on the surface. In one method, single-stranded nucleic acids are prepared and are attached to an epoxide surface on a glass slide by direct amine attachment at the 5' end of the template. A primer that specifically hybridizes to a primer attachment site on the template is added. Sequential exposure to deoxynucleotide triphosphates having an attached optically-detectable label is conducted. Direct amine attachment to the epoxide surface as described below in detail secures the oligonucleotide templates to the surface in a manner that is resistant to disruption in wash or nucleotide addition cycles. Additionally, the surface is treated with a blocking agent to prevent non-specific binding of nucleotides, label, and debris on the surface. Preferred blocking strategies for nucleic acids include covalent attachment of molecules to the surface that create a neutral or hydrophylic environment on the surface. Especially preferred are those that create a net negative charge on the surface. For example, treatment of the surface with Tris, phosphates, amines, and other entities that do not create an optical signal, that create the appropriate charge environment on the surface, and/or that "out-compete" non-specific binders for adherence to the surface are preferred. Finally, active rinse agents include components that displace non-specifically-bound entities. In this case, hydrophobic molecules, such as acetonitrile, are preferred as described below. Citrate-containing buffers are also useful to reduce non-specific binding and to promote adherence of reactive species (i.e., template/primer duplex).

In an alternative embodiment, methods of the invention are also useful to create surfaces that favor specific protein-protein interactions. For example, surfaces are coated with specific antibodies (either homogeneous or heterogeneous populations), and various antigenic interactions are probed by introduction of antigenic material to the surface. In that case, the surface is treated to induce charge that is consistent with retention of specific proteins but that disrupts surface interactions of non-specifically bound material. Accordingly, for hydrophobic proteins, similar conditions as described above are applicable. For hydrophilic proteins, opposite conditions are useful (e.g., non-neutral, or positively-charged blocking agents).

There are numerous methods according to the invention for preparing substrates to achieve the combination of reduced background and increased resolution of detection. For example, there are numerous alternative substrates that are useful, depending upon the molecular species to be attached. A relatively clean substrate is one that contains little or no foreign matter that might generate detectable radiation. Glass and fused silica, prepared as described below, are useful.

Surface coatings are also important. In one embodiment, a surface comprising a fluoropolymer, such as polytetrafluoroethylene (Teflon) is applied to the substrate. Such a surface emits little background radiation because very few particles stick to the surface. There also are numerous ways to treat a surface to remove defects that are ultimately responsible for the production of background. Such methods are contemplated herein and described in detail below. They include, for example, treating the surface of a substrate with a coating or film to remove surface defects.

In one preferred method, the invention generally contemplates coating a substrate with an epoxide. The substrate is further exposed to a blocking agent that inhibits non-specific binding of molecules to the substrate. Inhibiting non-specific binding of molecules on the substrate reduces background signal that interferes with detecting incorporation events during nucleic acid sequencing. Examples of blocking agents include water, Tris, sulfate, amines, phosphates ($PO_4$) and detergents.

The invention is especially useful for the attachment of nucleic acids to a surface. In a preferred embodiment, nucleic acid is attached to an epoxide on the surface. Nucleic acid can be attached directly via an amine linkage that reacts with the closed epoxide loop or via a linker, such as streptavidin, that has been reacted with the epoxide surface. When using epoxide, it is important that the surface be comprised mainly of unreacted epoxide. Reacted epoxide will form an alcohol on the surface which will have difficulty reacting with linker molecules. Other examples of linkers include antigen/antibody, digoxigenin/anti-digoxigenin, dinitrophenol, fluorescein, and other haptens known in the art. Alternatively, nucleic acid template may contain other binding moieties that result in a conformational change of the epoxide ring and result in a direct attachment of the template to the opened epoxide ring. For example, in some embodiments, templates comprise an amine group that covalently bonds to epoxide.

In some embodiments, epoxide is attached to a substrate via a silica coating. Epoxide can be attached through silanization techniques known in the art. For example, in some embodiments, epoxide is covalently attached to a substrate in the substantial absence of an aromatic solvent. Any other molecule capable of linking an epoxide to a substrate also is contemplated by the invention. Finally, electrostatic charge differences may allow for direct linkage to a substrate, either through covalent bonding or ionic interactions.

In a preferred embodiment, the substrate comprises a layer of epoxide molecules arranged in a uniform way, for example, to form a monolayer. In some embodiments, which may include any of the elements described above or below, it is advantageous to block non-specific binding sites that may interfere with detection of incorporation events during nucleic acid sequencing reactions. Agents such as water, sulfite, an amine group, a phosphate or a detergent may be used to block non-specific binding. A detergent, such as Tris, can serve to block or passivate the epoxide molecules alone or in conjunction with other blocking agents. Thus, a detergent may be incorporated into surface washing steps in order to preserved a passivated surface and prevent excess background that may interfere with detection. Blocking can occur by exposing the surface to molecules that compete with non-specific binders or, on an epoxide or other reactive surface, that react to reduce or eliminate the reactive portion of the surface molecule. For example, water can open the epoxide ring, making it less reactive. Thus, after attachment of oligonucleotides, an epoxide surface can be rinsed in order to reduce or eliminate the reactive functionality of the epoxide, thus reducing non-specific binding.

Methods of the invention also optionally include a surface drying step. In some embodiments, the surface is exposed to a drying agent prior to, during and/or after a chemical reaction, such as a nucleotide incorporation step. Examples of preferred drying agents include, without limitation, phosphate buffer, an alcohol (such as, for example, EtOH), air and/or $N_2$.

In a preferred embodiment, methods of the invention are used to prepare and treat surfaces for single molecule sequencing. As noted above, single molecule sequencing differs from traditional bulk sequencing, inter alia, in that in single molecule, individual nucleic acid duplex are analyzed, which leads to the ability to individually resolve genomic differences across individuals, to analyze individual tumors, and to assess individual affects of treatment, lifestyle, etc. on health and disease. Single molecule sequencing requires particular attention to signal resolution. In a typical single molecule reaction, individual nucleotide triphosphates, having an optically-detectable label (e.g., a fluorescent molecule) attached, are added in a template-dependent fashion to the primer portion of a duplex as described above. Individual labels are imaged upon incorporation, and a sequence is compiled based upon the sequential addition of bases to the primer.

It also has been discovered that in a nucleic acid sequencing reaction utilizing surface-bounds templates and fluorescent labels, the efficiency of base-over-base incorporation is increased if photobleaching is minimized or eliminated altogether. Thus, preferred methods of the invention are conducted under conditions that reduce, minimize, or eliminate bleaching of fluorescent label.

When sequencing at the single molecule level, templates should remain as stationary and stable on the substrate as possible. If an epoxide surface is used, several linkage strategies are possible in order to achieve stability. A direct amine linkage is useful. Other, indirect, linkages may also be used. For example, a biotin/streptavidin (or avidin) linkage or an antibody/antigen linkage is beneficial as an attachment mechanism. Nucleic acids may also be attached to a surface via a "sandwich" between two reactive species (e.g., biotin-avidin-biotin and the like). Regardless of the mechanism for attachment, the surface is then blocked with a blocking agent to reduce background. By modifying the pH of the solution or the salt concentration, the binding properties of the molecules may be altered such that binding of the nucleic acid template to the substrate may be favored or inhibited. Generally, increasing the pH of the solution facilitates the binding of the nucleic acid template to a biotin/streptavidin complex. On the other hand, decreasing the pH of the solution inhibits the binding of the nucleic acid template to the biotin/streptavidin complex.

As indicated above, a stationary and stable template is preferred for sequencing. As such, the invention provides various primer/template anchoring methods. One advantage of anchoring methods provided herein is the ability to reproducibly attach to a surface a nucleic acid to be sequenced. Generally, methods of the invention include the use of polynucleotide regions at or near the anchoring site in order to stabilized hybridized duplex. Methods further include the addition of locked nucleic acids (LNA) to further stabilize the duplex.

The invention is useful for conducting a number of different chemical reactions. For example, protein-protein interactions, such as receptor binding studies, enzyme activity, and the like are enhanced by surface preparation and treatment methods described herein. In a preferred embodiment, the invention is applied to sequencing nucleic acids, and especially to sequencing nucleic acids at the single molecule level. The invention is useful in sequencing any form of nucleic acid, such as double-stranded DNA, single-stranded DNA, single-stranded DNA hairpins, DNA/RNA hybrids, and RNA. Nucleotides useful in the invention include any nucleotide or nucleotide analog, whether naturally-occurring or synthetic. For example, preferred nucleotides are adenine, cytosine, guanine, uracil, or thymine bases. Also included are nucleotide analogs, such as methylated nucleic acids, peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, including chain-terminating analogs.

Nucleotides particularly useful in the invention comprise detectable labels. Labeled nucleotides include any nucleotide that has been modified to include a label that is directly or indirectly detectable. Preferred labels include optically-detectable labels, including fluorescent labels or fluorophores, such as fluorescein, rhodamine, cyanine, cyanine-5 dye, cyanine-3 dye, or a derivative or modification of any of the foregoing, and also include such labeling systems as hapten labeling. Accordingly, methods of the invention further provide for exposing the primer/target nucleic acid complex to a digoxigenin, a fluorescein, an alkaline phosphatase or a peroxidase.

The invention is particularly useful in high throughput sequencing of single molecule nucleic acids in which a plurality of target nucleic acids are attached to a solid support in a spatial arrangement such that each nucleic acid is individually optically resolvable. As described herein, in a preferred embodiment, a substrate-bound primer/target nucleic acid complex is bound to and epoxide surface. A sequence is determined by detecting the incorporation of a nucleotide, repeating the exposing and detecting steps, and compiling a sequence of the template based upon the order of incorporated nucleotides.

Preferred substrates include glass, polished glass, silica, fused silica, plastic and gels. Examples of substrates appropriate for the invention also include polytetrafluoroethylene or a derivative of polytetrafluoroethylene, such as silanized polytetrafluoroethylene. In a particularly preferred embodiment, the substrate comprises a silica coating.

Functionalized surfaces for oligonucleotide attachment also are contemplated by the invention. For example, functionalized silicon surfaces are prepared by UV-mediated attachment of alkenes to the surface. UV light mediates the reaction of t-butyloxycarbonyl (t-BOC) protected omega-unsaturated aminoalkane (10-aminodec-1-ene) with hydrogen-terminated silicon. Removal of the t-BOC protecting group yields an aminodecane-modified silicon surface. Nucleotide arrays are prepared by coupling the amino groups to thiol-modified oligodeoxyribonucleotides using a heterobifunctional crosslinker. The surface density of oligonucleotides may be controlled by adjusting the amount of aminoalkane used. A linear relationship between the mole fraction of aminodecen and the density of hybridization sites has been found. Alternatively, less than all the t-BOC protecting groups are removed prior to nucleic acid exposure.

In one embodiment, fluorescence resonance energy transfer (FRET) as a detection scheme. Fluorescence resonance energy transfer in the context of sequencing is described generally in Braslavasky, et al., *Sequence Information can be Obtained from Single DNA Molecules*, Proc. Nat'l Acad. Sci., 100: 3960-3964 (2003), incorporated by reference herein. Essentially, in one embodiment, a donor fluorophore is attached to the primer, polymerase, or template. Nucleotides added for incorporation into the primer comprise an acceptor fluorophore that is activated by the donor when the two are in proximity. Activation of the acceptor causes it to emit a characteristic wavelength of light. In this way, incorporation of a nucleotide in the primer sequence is detected by detection of acceptor emission. Of course, nucleotides labeled with a donor fluorophore also are useful in methods of the invention; FRET-based methods of the invention only require that a donor and acceptor fluorophore pair are used, a labeled nucleotide may comprise one fluorophore and either the template or the polymerase may comprise the other. Such labeling techniques result in a coincident fluorescent emission of the labels of the nucleotide and the labeled template or polymerase, or alternatively, the fluorescent emission of only one of the labels.

In a preferred embodiment, after detection, the label is rendered undetectable by removing the label from the nucleotide or extended primer, neutralizing the label, or masking the label. In certain embodiments, methods according to the invention provide for neutralizing a label by photobleaching. This is accomplished by focusing a laser with a short laser pulse, for example, for a short duration of time with increasing laser intensity. In other embodiments, a label is removed from its nucleotide by photocleavage. For example, a light-sensitive label bound to a nucleotide is photocleaved by focusing a particular wavelength of light on the label. Generally, it may be preferable to use lasers having differing wavelengths for exciting and photocleaving. Labels also can be chemically cleaved. Labels may be removed from a substrate using reagents, such as NaOH, dithiothreitol, or other appropriate buffer reagent. The use of disulfide linkers to attach the label to the nucleotide are especially useful and are known in the art.

As described herein, the invention promotes stable attachment of target molecules to a prepared surface. Generally, the invention comprises surfaces that promote secure attachment of reactive molecules with reduced or eliminated non-specific binding, and that are susceptible to effective rinsing. Methods of the invention comprise exposing a surface to a reactive molecule and an agent that inhibits non-specific binding of molecules to the substrate, conducting a chemical reaction involving the attached molecules, and rinsing unbound reactants effectively from the surface.

In a preferred embodiment, attachment occurs via covalent bonding of the molecule of interest to the surface. Attachment may be via a chemical linkage, as between biotin and avidin or streptavidin, or may be via attachment to embedded binding molecules, such as silanes and others that promote molecular attachment to the surface. For example, oligonucleotides modified with an $NH_2$-group are immobilized onto epoxy silane-derivatized or isothiocyanate-coated glass slides. Succinylated nucleic acids may also be coupled to aminophenyl- or aminopropyl-derivatized glass slides by peptide bonds, and disulfide-modified nucleic acids can be immobilized onto a mercaptosilanised glass support by a thiol/disulfide exchange reaction. Alternatively, unactivated microscope slides may be used with activated, silanised nucleic acids. Many attachment strategies are based on heterobifunctional crosslinking molecules, providing numerous alternatives for both the linking molecule and the nucleic acids itself.

In a particular embodiment, methods according to the invention provide for conducting a chemical reaction on a substrate for detection of single molecules thereon. Such methods include the steps of treating a substrate to remove surface defects and covalently linking a plurality of molecules to the substrate such that members of the plurality of molecules are individually optically resolvable. Preferably, the molecule is a nucleic acid, such as DNA or RNA. Also, in some embodiments, methods according to the invention include a treating step that can include removing surface defects on a substrate by applying a chemical layer to the substrate. In some embodiments, a chemical layer can further include nucleotides. Generally, the surface for detection of single molecules includes a coating or film that is resistant to chemical bonding but that is accommodating for anchoring a molecule to be detected, such as a nucleic acid. Methods also include washing the substrate in order to remove substantially debris without disturbing attached molecules.

In another aspect, methods for optically detecting a single nucleic acid molecule on a substrate include the steps of preparing a substrate to reduce background optical radiation emanating from the substrate to less than an amount that exceeds a signal to be detected, and adhering to the substrate a plurality of nucleic acid molecules. Methods according to this aspect of the invention further include exposing the nucleic acid molecules to a polymerase and at least one nucleic acid base comprising a detectable label under conditions that allow incorporation of the base into the nucleic acid molecule. In addition, methods according to the invention include observing the detectable label as a distinct signal on the substrate, thereby to detect a single nucleic acid molecule bound to the substrate.

In another aspect of the invention, a substrate is coated with a polyelectrolyte multilayer. As such, methods for sequencing a target nucleic acid by synthesizing a complementary strand can include the steps of coating a surface of a substrate with a polyelectrolyte multilayer; permitting localization of a target nucleic acid on the surface of said substrate; providing a nucleotide including a labeling moiety; and allowing incorporation of the nucleotide into the complementary strand in the presence of a polymerase. Methods according to the invention further include detecting incorporation of the nucleotide into the complementary strand to determine the sequence of the target nucleic acid. Methods may also be used in kits designed to carry out and facilitate the methods provided herein.

A further embodiment for preparing surfaces for single molecule detection comprises the covalent application on a surface (e.g., glass) of a charge layer, upon which an electrolyte layer is built. The covalent binding of the initial charge layer facilitates the ability of the overall charge layer (e.g., a PEM) to stick to the surface (i.e., the rinsability is improved). For example, an amine layer covalently attached to glass improves the ability of the surface attachment layer to adhere to glass. Thus, a PEM can be built on the amine layer that is wash-resistant compared to a non-covalently linked PEM. In one embodiment, the invention comprises the use of polydimethylsiloxane over which is flowed a solution of diacrylated polyethylene glycol (e.g., DAPEG SR610, Sartomer Corp. Exton, Pa.) and hexachloroplatinate (Aldrich) in a volumetric ration of about 200:1. The surface is then baked at about 80° C. for about 30 minutes, and the surface is rinsed with water to remove the diacrylated polyethylene glycol. A PEM, comprising alternating layers of polyethyleneimine and polyacrylate is then layered over the surface. Finally, the surface is coated with biotin followed by streptavidin in order to create binding sites for biotinylated nucleic acids.

An alternative surface chemistry comprises preparing a surface as described herein, but instead of applying a polyelectrolyte multilayer, a coating of a negatively-charged coupling protein is applied. For example, biotin sulfate or another biotin derivative that contains a negative charge is added to the surface. The negative charge on the coupling protein serves the same effect as the PEM The coupler, for example biotin sulfate, is then bound to streptavidin for coupling to biotinylated nucleic acids.

As will be appreciated by one skilled in the art, individual features of the invention may be used separately or in any combination. A detailed description of embodiments of the invention is provided below. Other embodiments of the invention are apparent upon review of the detailed description that follows.

DETAILED DESCRIPTION OF THE INVENTION

Figure 1:
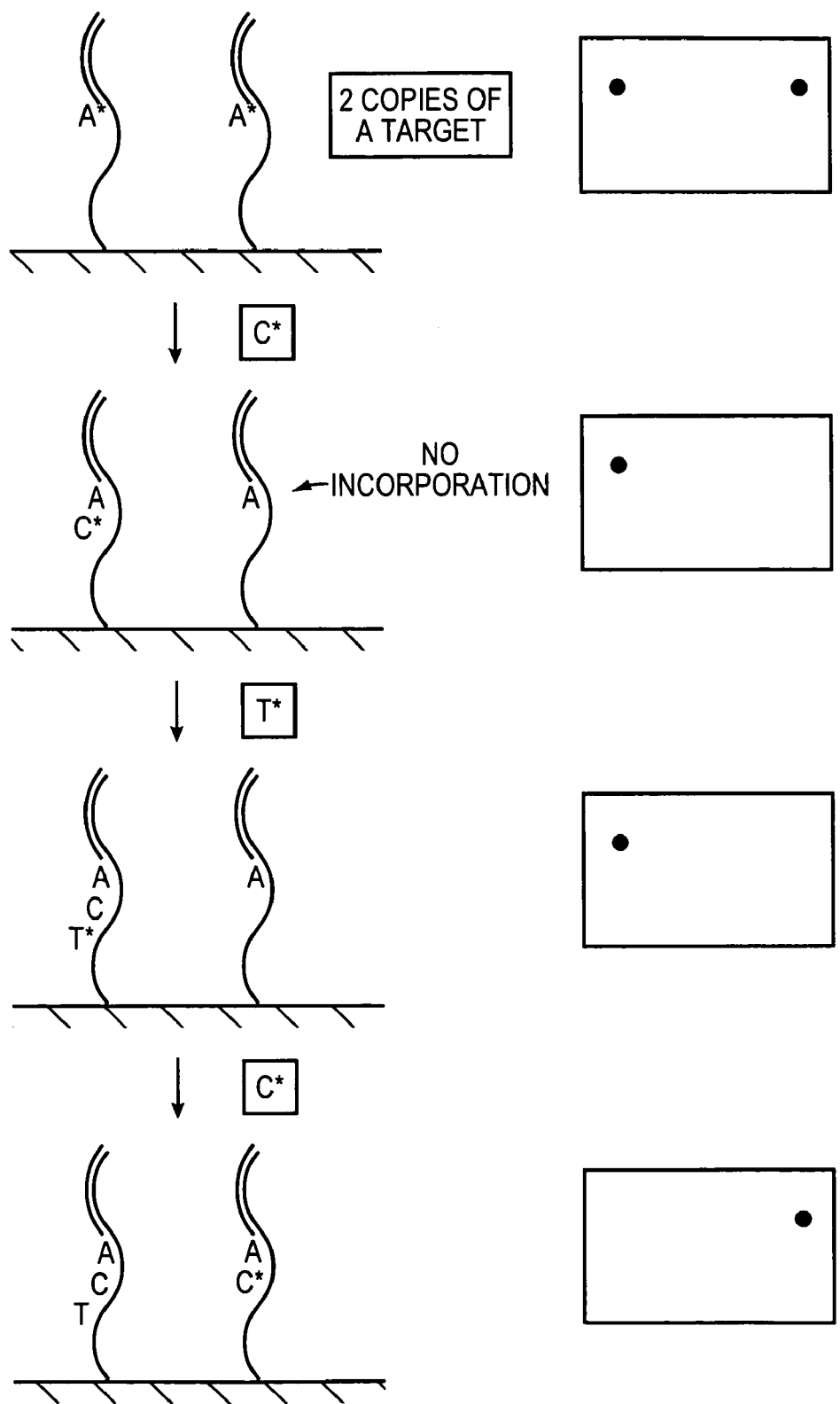
FIG. 1 depicts single molecule sequencing of a target nucleic acid strand randomly anchored to a substrate or support.

The surface chemistries provided by methods and devices of the invention provide numerous advantages for applications involving surface-bound chemical reactions. The invention is especially useful in applications in which high signal-to-noise is beneficial, such as in single molecule detection. In some applications, a surface is pretreated to create a surface chemistry that facilitates nucleic acid attachment with single molecule resolution, where the nucleic acid molecules are available for subsequent synthesis reactions. In addition, treating the substrate with a coating or film (e.g., epoxide, PEM and other techniques described herein) can be significant for determining the sequence of a single molecule nucleic acid attached thereto.

Surface chemistries of the present invention also facilitate the surface attachment of reactive molecules. For example, a negatively-charged surface layer facilitates attachment of nucleic acid molecules. Attachment can be covalent or non-covalent. Carboxylic acids, for example, are good targets for covalent bond formation. In some embodiments, a binding pair may be used, where a terminal layer bears one member of the pair, and the nucleic acid molecule bears the other. For example, biotin may be coupled to a terminal layer of the substrate to facilitate anchoring using biotin-streptavidin binding pairs. Such treatment allows a high density of nucleic acid coverage with single molecule resolution as described in more detail below.

The invention will be exemplified in the context of nucleic acid sequencing, but as will be apparent to the skilled artisan, the invention is applicable to any chemical reaction involving surface-bound reactants.

The present invention provides appropriate surfaces and a strong template-to-substrate anchoring systems that have greatly reduced non-specific binding on the surface. In particular, single molecule sequencing reactions benefit from high surface stability, efficient washing, and the ability to repel non-specific binding. As such, embodiments of the invention provide for a substrate that forms wash-resistant chemical interactions with nucleic acid templates and is also blockable so that once a nucleic acid template is bound to the surface, the surface is treated to reduce non-specific binding. Many surfaces known in the art are suitable to bind a nucleic acid template, however, many of those same surfaces are not suitable for single molecule sequencing due to high non-specific binding of non-target molecules, which interferes with later detection of incorporation events during sequencing.

I. Surfaces

According to the invention, surfaces are prepared that facilitate attachment of reactive species and that have low background. A preferred surface is treated to remove defects that are responsible for the production of background that can interfere with detection of surface chemical events (e.g., incorporation of nucleotides). As such, substrates according to the invention can be treated, associated or chemically modified with one or more coatings or films that increase binding affinity or improve localization of the bound reactants. Increased surface binding affinity also leads to increased surface retention, maximizing the availability of reactants on the surface. Exemplary films or coatings include epoxides, including those that are derivatized (e.g., with a binding molecule, such as streptavidin).

As discussed herein, not only can a surface be treated to remove defects that are responsible for the production of background, a surface can be treated to improve the positioning of target molecules, such as nucleic acids, for analysis. As such, a substrate according to the invention can be treated with one or more charge layers (e.g., a negative charge) to repel a charged molecule (e.g., a negatively charged labeled nucleotide). For example, a substrate according to the invention can be treated with polyallylamine followed by polyacrylic acid to form a polyelectrolyte multilayer. The carboxyl groups of the polyacrylic acid layer are negatively charged and thus repel negatively charged labeled nucleotides, improving the positioning of the label for detection.

In some embodiments, the substrates (e.g., glass slides) are associated or derivatized with one or more coatings and/or films that increase molecule-to-substrate binding affinity (e.g., target nucleic acid-to-glass). Increased molecule-to-substrate binding affinity results in increased molecule retention during the various stages of substrate preparation and analysis (e.g., hybridization, staining, washing, scanning stages, and the like, of preparation and analysis). Additionally, any coatings or films applied to the substrate should be able to withstand subsequent treatment steps (e.g., photoexposure, boiling, baking, soaking in warm detergent-containing liquids, and the like) without substantial degradation or disassociation from the substrate.

Examples of substrate coatings and films include, vapor phase coatings of 3-aminopropyltrimethoxysilane, as applied to glass slide products, for example, from Molecular Dynamics, Sunnyvale, Calif. In addition, generally, hydrophobic substrate coatings and films aid in the uniform distribution of hydrophilic molecules on the substrate surfaces. Importantly, in those embodiments of the invention that employ substrate coatings or films, the coatings or films that are substantially non-interfering with primer extension and detection steps are preferred. Additionally, it is preferable that any coatings or films applied to the substrates either increase target molecule binding to the substrate or, at least, do not substantially impair target binding.

Other approaches to coat or film substrates comprise associating chemical agents to the substrate, whereby the coating or film is selected for their reactivity with molecules or nucleic acid targets. For example, organo-amine and organo-aldehyde reactive groups at a concentration of about $5 \times 10^{12}$ reactive groups/$cm^2$, for example, can be applied to a substrate. These reactive groups increase the binding affinity of nucleic acids, proteins, small molecules, extracts, and whole or fragmented cells, etc. to substrates. Substrate coatings and films are preferentially applied as monolayers, however more than one layer can be applied as appropriate. In some embodiments of the present invention, the substrates are fabricated using photolithographic technologies. Maskless substrate fabrication technology is also known in the art.

In one aspect, preferred embodiments of the invention include the use of a surface that comprises an epoxide. An epoxide is an ether in which oxygen is part of a three-member ring structure that is under conformational strain. An epoxide is a more reactive than other ethers due to the strained ring structure.

As discussed herein, a nucleic acid can be directly or indirectly linked to an epoxide on the surface of a substrate. In a direct attachment embodiment, the epoxide is introduced to a template nucleic acid bearing an amine group. The highly-reactive epoxide ring opens, and a reactive carbon binds to the amine group on the template. Unfortunately, the same properties that make the epoxide reactive to an amine group on the nucleic acid template, also make the epoxide reactive to other molecules, thereby increasing the likelihood of non-specific binding. In order to inhibit non-specific binding of molecules to a surface comprising an epoxide during nucleic acid sequencing reaction, epoxides not bound to nucleic acid templates should be passivated.

Any molecule capable of interacting with or breaking the epoxide ring, or binding to available carbons in an already-broken epoxide ring, may be appropriate as a passivating agent. A preferred passivating (blocking) agent should not interfere with intended surface chemistry (e.g., incorporation of a nucleotide or determining/detecting the incorporated nucleotide.) examples of preferred blocking agents for use in the invention are water, a sulfate group, an amine group, a phosphate ($PO_4$) or a detergent (such as Tris). Blocking agents may be introduced or reintroduced at any time during the sequencing procedure. Also, in some embodiments, blocking agents may be used to pre-treat the surface of the substrate prior to exposing the substrate to a nucleic acid template. In addition, blocking agents, such as a detergent (e.g., Tris) may be included in some or all wash steps in order to passivate the surface during incubation periods and/or washes.

In a preferred embodiment, the surface of a substrate is coated with an epoxide monolayer. An epoxide monolayer may be deposited onto a surface by many methods known in the art, including silanization. Different molecules or combinations of molecules may serve to link the epoxide to a surface. Ideally, a surface will be coated with an even distribution of epoxides prior to template introduction. In a preferred embodiment, nucleic acids (double- or single-stranded) are then introduced to the epoxide layer. The amine reacts with the epoxide ring, which results in a direct link between the nucleic acid and the epoxide. Blocking of unbound epoxides then can be performed.

As discussed, a nucleic acid also can be indirectly linked to an epoxide on the surface of a substrate. In one embodiment, the nucleic acid is linked to an epoxide that has been exposed to a biotinylated amine. Upon exposure, the amine reacts with the epoxide ring, and therefore, links the biotin to the epoxide. The biotinylated epoxide is further exposed to streptavidin to coat the substrate. A biotinylated nucleic acid template then is introduced to the substrate. Blocking of any unbound epoxide on the surface can be accomplished using any of the methods according to the invention described herein.

Surface charge affects the surface stability of a nucleic acid. The effectiveness of performing substrate-based sequencing in general, and single molecule sequencing in particular, depends in part on the conformation of the nucleic acid template on the substrate. During a sequencing reaction, for example, the steric conformation of the nucleic acid template is an important factor for successful primer annealing and primer extension. Although a negatively charged nucleic acid template molecule tends to repel from a negatively charged substrate thereby making attachment of the nucleic acid template to the surface of the substrate more difficult. Once a nucleic acid template is bound to the surface of a substrate, a negative charge on the substrate promotes the proper conformation of the nucleic acid for sequencing purposes. Namely, a negatively charged surface helps repel the nucleic acid template from the surface, projecting the template away from the surface (or substantially orthogonal to a horizontal surface) and making the nucleic acid template more available to reagents such as a primer, polymerase and/or nucleotides (labeled or unlabeled.)

As a result, according to the invention, surface charge can be manipulated to achieve ideal conditions during template attachment and primer extension. For example, during the loading phase where the template is bound or positioned on the surface, the salt concentration of the solution may be increased in order to create a more positive surface charge on the substrate to facilitate reaction between the amine portion of the nucleic acid and the epoxide ring. Conversely, after the nucleic acid has been secured to the surface, the salt concentration of the solution can lowered in order to repel the nucleic acid template from the surface of the substrate thereby sterically conforming the nucleic acid strand for primer annealing and extension.

In another aspect, the invention provides a substrate including a layer of polyanions and nucleic acid molecules anchored on the layer of polyanions. Accordingly, nucleic acid molecules are positioned to avoid being substantially parallel (e.g., is hindered from lying down on the layer of polyanions.) In some embodiments, the surface of a substrate is pretreated to create a surface chemistry that facilitates nucleic acid molecule attachment and subsequent sequence analysis. In some of these embodiments, the substrate surface is coated with a polyelectrolyte multilayer (PEM). In some cases, biotin can be applied to the PEM, followed by application of streptavidin. The substrate can then be used to attach biotinylated nucleic acids.

The PEM-coated substrate provides substantial advantages for nucleic acid sequence determination and for polymerization reactions. First, a PEM can easily be terminated with polymers bearing carboxylic acids, thereby facilitating nucleic acid attachment. Second, the attached nucleic acid molecule is available for extension by polymerases due to the repulsion of like charges between the negative carboxylic groups. Also, the negative nucleic acid backbone hinders the nucleic acid molecule from a formation that is substantially parallel to the surface of the substrate. In addition, the negative charges repel unincorporated nucleotides, thereby reducing nonspecific binding and hence background interference.

In some embodiments, multiple layers of alternating positive and negative charges are used. In the case of incompletely-charged surfaces, multiple-layer deposition tends to increase surface charge to a well-defined and stable level. For example, surfaces can be coated with a PEM for attachment of target nucleic acids and/or primers via light-directed spatial attachment. Alternatively, target nucleic acids and/or primers can be attached to a PEM-coated surface chemically. PEM formation has been described in Decher et al. (Thin Solid Films, 210:831-835, 1992). PEM formation proceeds by the sequential addition of polycations and polyanions, which are polymers with many positive or negative charges, respectively. Upon addition of a polycation to a negatively-charged surface, the polycation deposits on the surface, forming a thin polymer layer and reversing the surface charge. Similarly, a polyanion deposited on a positively charged surface forms a thin layer of polymer and leaves a negatively charged surface. Alternating exposure to poly(+) and poly(−) generates a polyelectrolyte multilayer structure with a surface charge determined by the last polyelectrolyte added. This can produce a strongly-negatively-charged surface, repelling the negatively-charged nucleotides.

Detailed procedures for coating a substrate with PEM for immobilizing nucleic acid are described below. In general, the surface of the substrate (e.g., a glass cover slip) can be cleaned with a RCA solution. After cleaning, the substrate can be coated with a PEM, terminating with carboxylic acid groups. Following biotinylation of the carboxylic acid groups, streptavidin can be applied to generate a surface capable of capturing biotinylated molecules. Biotinylated nucleic acid templates or primers can then be added to the coated substrate for anchoring. During the immobilization or anchoring step, a high concentration of cations, e.g., $Mg^{2+}$, can be used to screen the electrostatic repulsion between the negatively-charged nucleic acid molecules and the negatively-charged PEM surface. In subsequent steps, the cation concentration can be reduced to re-activate repulsive shielding. By titrating biotinylated nucleic acid molecules, it is possible to bind such a small number of molecules to the surface that they are separated by more than the diffraction limit of optical instruments and thus able to be visualized individually.

The attachment scheme described here can be readily generalized. Without modification, the PEM/biotin/streptavidin surface produced can be used to capture or immobilize any biotinylated molecule. A slight modification can be the use of another capture pair, for example, substituting digoxygenin (dig) for biotin and labeling the molecule to be anchored with anti-digoxygenin (anti-dig), or dinitrophenol and its antibody can be used. Reagents for biotinylation or dig-labeling of amines are both commercially available.

Attachment chemistry is nearly independent of the underlying surface chemistry and so permits further generalization. Glass, for instance, can support PEMs terminated with either positive or negative polymers, and a wide variety of chemistry is available for either. But other substrates such as silicone, polystyrene, polycarbonate, etc. or even membranes and/or gels, which are not as strongly charged as glass, can still support PEMs. The charge of the final layer of PEMs on weakly-charged surfaces becomes as high as that of PEMs on strongly-charged surfaces, as long as the PEM has a sufficient number of layers. Thus, advantages of the glass/PEM/biotin/streptavidin/biotin-nucleic acid surface chemistry can readily be applied to other substrates. In some embodiments, the attachment schemes can be either ex-situ or in-situ.

In another aspect of the invention, the substrate may be prepared by, for example, coating with a chemical that increases or decreases hydrophobicity or coating with a chemical that allows covalent linkage of the nucleic acid molecules or other polymeric sequences. Some chemical coatings may both alter the hydrophobicity and allow covalent linkage. Hydrophobicity on a solid substrate may readily be increased by silane treatment or other treatments known in the art. Linker molecules adhere to the surface and comprise a functional moiety that reacts with biomolecules. Many such linkers are readily available and known in the art. For example, substrates or supports are modified with photo-labile-protected hydroxyl groups, alkoxy or aliphatic derivatized hydroxyl groups, or other chemicals.

A preferred coating that both decreases hydrophobicity and provides linkers is poly(ethyleneimine). In addition, poly (ethyleneimine) (PEI) coated solid substrates also have the added benefit of long shelf life stability. The coating of silicon wafers and glass slides with polymers such as poly(ethyleneimine) can be performed in-house or through companies such as Cel Associates (Houston, Tex.). Glass slides also can be coated with a reflective material or coated with PEI using silane chemistry. The PEI coating permits the covalent attachment of single or double stranded nucleic acids, single or double stranded long DNA molecules or fragments or any other amine-containing biomolecules to the substrate or support. Nucleic acids may be covalently attached at the 5' using a hexylamine modification, which places a primary amine at the 5'-end of the oligonucleotide. The 5'-amine on the oligonucleotide may then be reacted with a cross-linker, such that the oligonucleotide is covalently attached to the polymer coating on the solid support.

Generally, a substrate may be of any suitable material that allows for single molecules to be individually optically resolvable. Substrates for use according to the invention can be two- or three-dimensional and can comprise a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly (methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

The invention also includes three-dimensional substrates such as, for example, spheres, tubes (e.g., capillary tubes), microwells, microfluidic devices, or any other structure suitable for anchoring a nucleic acid. For example, a substrate can be a microparticle, a bead, a membrane, a slide, a plate, a micromachined chip, and the like. Substrates can include planar arrays or matrices capable of having regions that include populations of target nucleic acids or primers. Examples include nucleoside-derivatized CPG and polystyrene slides; derivatized magnetic slides; polystyrene grafted with polyethylene glycol; and the like.

Generally, a substrate may be of any suitable material that allows for single molecules to be individually optically resolvable. As such, devices and methods according to the invention can resolve one molecule from another. For example, the detection limit can be in the order of a micron. This implies that two molecules can be a few microns apart and be resolved, that is individually detected and/or detectably distinguished from each other. Factors for selecting substrates include, for example, the material, porosity, size, and shape. In addition, substrates that can lower (or increase) steric hindrance of polymerase are preferred according to the invention. Other important factors to be considered in selecting appropriate substrates include size uniformity, efficiency as a synthesis support, and the substrate's optical properties, e.g., clear smooth substrates (free from defects) provide instrumentational advantages when detecting incorporation of nucleotides in single molecules (e.g., nucleic acids).

Preferably, a substrate used according to the invention includes a biocompatible or biologically inert material that is transparent to light and optically flat (i.e., with a minimal micro-roughness rating). Specially manufactured, or chemically derivatized, low background fluorescence substrates (e.g., glass slides) are also contemplated according to the invention. Substrates may be prepared and analyzed on either the top or bottom surface of the planar substrate (i.e., relative to the orientation of the substrate in the detection system.) In addition, a substrate should have minimal defects that are responsible for the production of background that might interfere with detection of incorporated nucleotides. As such, a substrate can be pre-treated with a biocompatible or biologically inert material that creates a planar surface free from defects prior to use in the attachment and/or sequencing methods discussed herein.

II. Attaching, Blocking, and Rinsing

A. Direct and Indirect Attachment of Streptavidin to Epoxysilane Surfaces.

Methods. Glass surfaces with a uniformly deposited reactive epoxysilane coating is purchased from Erie Scientific Company, Portsmouth, N.H. and used without further modification. For direct attachment of streptavidin, the surfaces are reacted, resulting in the random cross-linking of amino groups on the surface of the protein with epoxide groups on the surface of the glass. The surfaces are incubated with streptavidin at a concentration of 170 ug/ml in 150 mM K2PO4 (pH 8.5) at room temperature for 30 minutes. After incubation with streptavidin, the excess streptavidin is removed by extensive rinsing in 150 mM K2PO4 (pH 8.5) followed by 3×SSC, 0.1% Triton, followed by rinsing in 3×SSC, followed by storage in 150 mM K2PO4. Indirect attachment of streptavidin is accomplished through a heterofunctional poly(ethylene glycol). A 10% w/v solution of linear HCl—NH2-PEG-COOH MW 3400 (Nektar Therapeutics, Huntsville, Ala.) is reacted with the epoxysilane surface in 150 mM K2PO4 (pH 8.5) at room temperature for varying times to insure adequate coverage. After the reaction, excess PEG is removed by extensive rinsing in the same solutions described above. After the blocking of the residual epoxide functionality as described below in Part B, streptavidin is covalently attached to the pendant carboxylic acid groups of the PEG by NHS-EDC mediated coupling. A solution of 200 mM N-hydroxy succinamide, 200 mM EDC) is prepared fresh (immediately before using) in 0.1 M MES (pH 5.5), 0.5 M NaCl. The PEG treated surface is pre-treated for 10 minutes at room temperature in 0.1 M MES (pH 5.5), ), 0.1M NaCl and the surfaces are then transferred without drying to the NHS-EDC solution and activated for 15 minutes at room temperature. After rinsing in 0.1 M MES (pH 5.5), the surfaces are immersed with stirring in 0.14 mg/ml streptavidin in 0.1 M MES (pH 5.5), 0.1 M NaCl and allowed to react for 60 minutes at room temperature. Excess streptavidin is removed by rinsing in reaction buffer (minus streptavidin), followed by rinses with 3×SSC, 0.1% Triton.

B. Measuring the Effectiveness of Blocking of Residual Epoxide Functionality.

Methods. After the direct coupling of streptavidin or the coupling of the heterofunctional PEG, any residual epoxide functionality is blocked. In the case of the direct attachment of streptavidin, the choice of blocking groups serves as a layer that prevents the non-specific binding of fluorescent nucleoside triphosphates, but that does not destabilize the subsequent biotin binding capability of the tetrameric streptavidin. The first step is to determine how much, if any, residual reactive epoxy functionality has survived the two different streptavidin immobilizations by quantifying the amount of epoxide reactive Cyanine 5 labeled oligonucleotide that is able to react with or stick to the streptavidin treated-epoxysilane surface. A solution of 100 pM in 5'-Cy5-, 3'-aminohexyl oligonucleotide in 20 mm Tris-HCl, 50 mM NaCl, 0.001% Triton X-100 (pH 8.0) is incubated with the modified surfaces for 5 minutes, the excess labeled oligonucleotide is rinsed away with the reaction buffer minus oligonucleotide, followed by rinses with 3×SSC+0.1% Triton X-100, followed by rinses with reaction buffer minus the oligonucleotide. Replicate slides are then imaged.

The impact of different blocking strategies upon the non-specific absorption properties of the surface is determined by reacting the streptavidin modified surfaces (direct or PEGylated) with different blocking agents. Since fluorescently labeled nucleoside triphosphates are negatively charged at neutral pH, the impact of several neutral and negatively charged blocking agents are used. The following reagents are blocking reagents on both types of surfaces:

| 1 M | Tris 150 mM K2PO4 (pH 8.5) |
| 1 M | ethanolamine |
| 1 M | monofunctional PEG-NH2 MW 5000 |
| 1 M | glycine |
| 1 M | KHPO4 pH 8.5 |

Reacted slides are rinsed extensively with 150 mM K2PO4 (pH 8.5), followed by rinses with 3×SSC, followed by rinses with H2O. After blocking, the residual epoxide functionality is again be tested by challenging replicate slides of each of the streptavidin immobilization methods blocked with each of the reagents listed above. A solution of 100 pM 5'-Cy5-, 3'-aminohexyl oligonucleotide in 20 mm Tris-HCl, 50 mM NaCl, 0.001% Triton X-100 (pH 8.0) is incubated with the modified surfaces for 5 minutes, the excess labeled oligonucleotide rinsed away with the reaction buffer minus oligonucleotide, followed by rinses with 3×SSC+0.1% Triton X-100, followed by rinses with reaction buffer minus the oligonucleotide. Replicate slides are then imaged to determine the extent of blocking.

III. Sequencing

A target nucleic acid template can come from a variety of sources. For example, nucleic acid templates can be naturally occurring DNA or RNA isolated from any source, recombinant molecules, cDNA, or synthetic analogs, as known in the art. For example, the target nucleic acid template may be genomic DNA, genes, gene fragments, exons, introns, regulatory elements (such as promoters, enhancers, initiation and termination regions, expression regulatory factors, expression controls, and other control regions), DNA comprising one or more single-nucleotide polymorphisms (SNPs), allelic variants, and other mutations.

Nucleic acids templates can be obtained from any cell of a person, animal, plant, bacteria, or virus, including pathogenic microbes or other cellular organisms. Individual nucleic acids can be isolated for analysis. A target nucleic acid template for analysis may be obtained directly from a patient, e.g., from blood, urine, cerebrospinal fluid, seminal fluid, saliva, breast nipple aspirate, sputum, stool and biopsy tissue. Any tissue or body fluid specimen may be used according to methods of the invention.

Many methods are available for the isolation and purification of target nucleic acids for use in the present invention. Preferably, the target molecules or nucleic acids are sufficiently free of proteins and any other interfering substances to allow target-specific primer annealing and extension. Preferred purification methods include (i) organic extraction followed by ethanol precipitation, e.g., using a phenol/chloroform organic reagent, preferably using an automated DNA extractor, e.g., a Model 341 DNA Extractor available from PE Applied Biosystems (Foster City, Calif.); (ii) solid phase adsorption methods; and (iii) salt-induced DNA precipitation methods, such methods being typically referred to as "salting-out" methods. Optimally, each of the above purification methods is preceded by an enzyme digestion step to help eliminate protein from the sample, e.g., digestion with proteinase K, or other like proteases.

Target nucleic acids are immobilized on the surface of a substrate (e.g., a glass or plastic slide, a nylon membrane, or gel matrix). The target nucleic acid is hybridized to a primer to form a target nucleic acid-primer complex. Thereafter, primer extension is conducted to sequence the target nucleic acid or primer using a polymerase and a nucleotide (e.g., dATP, dTTP, dUTP, dCTP and/or a dGTP) or a nucleotide analog. Incorporation of a nucleotide or a nucleotide analog is detected at discrete locations on the surface. Nucleic acid-primer complex, as well as incorporated nucleotides, arte individually resolvable in single molecule embodiments. Alternatively, bulk signal from mixed nucleic acid populations or clonal populations of nucleic acids, are obtained.

Fast reagent application and removal is another advantage according to the invention. For example, concentrations of nucleotides and/or other reaction reagents can be alternated at different time points of the analysis. This could lead to increased incorporation rates and sensitivity. For example, when all four types of nucleotides are simultaneously present in the reaction to monitor dynamic incorporation of nucleotides, concentrations of the each of the respective nucleotides can be alternated between a first and a second range. This leads to both better visualization of the signals when low concentrations of nucleotides are present, and increased polymerization rate when higher concentrations of nucleotides are present.

Certain embodiments of the present invention avoid many of the problems observed with other sequencing methods. For example, the methods provided herein are highly parallel because many molecules can be analyzed simultaneously at high density (e.g., 1 or 2 million molecules per $cm^2$). Thus, many different nucleic acids can be sequenced or analyzed on a single substrate surface simultaneously according to methods and devices of the present invention.

Conditions for hybridizing primers to nucleic acid targets are well known. The annealing reaction is performed under conditions which are stringent enough to guarantee sequence specificity, yet sufficiently permissive to allow formation of stable hybrids at an acceptable rate. The temperature and length of time required for primer annealing depend upon several factors including the base composition, length and concentration of the primer, and the nature of the solvent used, e.g., the concentration of cosolvents such as DMSO (dimethylsulfoxide), formamide, or glycerol, and counterions such as magnesium. Typically, hybridization (annealing) with synthetic nucleic acids is carried out at a temperature that is approximately 5 to 10° C. below the melting temperature of the target-primer hybrid in the annealing solvent. Typically, the annealing temperature is in the range of 55 to 75° C. and the primer concentration is approximately 0.2 µM. Under such conditions, the annealing reaction is usually complete within a few seconds.

Methods according to the invention include conducting a chemical reaction involving at least one of the molecules and a first detectably-labeled moiety and observing the first detectably-labeled moiety in isolation from any other detectable-label present on the substrate.

Methods according to the invention also include conducting a primer extension reaction, such as exposing the nucleic acid to a primer under conditions sufficient to extend a nucleic acid by at least one base. Methods according to the invention also include the step of compiling a sequence of the molecule (nucleic acid) based upon sequential incorporation of the extension bases into the primer.

By anchoring the nucleic acids to the substrate, unincorporated nucleotides can be removed from the substrate by a washing step. In some embodiments, the substrate is made from fused silica slide (e.g., a fused silica glass slide from Esco, Cat. R130110). Compared to some other substrate materials (e.g., a regular glass slide), fused silica has very low auto-fluorescence, that may be desirable in certain embodiments.

Various configurations are possible according to methods and devices of the invention. In some embodiments, the target nucleic acids are immobilized to the surface prior to hybridization to the primer. Alternatively, the target nucleic acid can be hybridized to the primers first and then immobilized on the surface. In other embodiments, the primers may be immobilized to the surface, and the target nucleic acids are then attached to a substrate through hybridization with the primers. The primer may be hybridized to target nucleic acid prior to providing nucleotides or nucleotide analogs for the polymerization reaction or the primer may be hybridized to the target nucleic acid while the nucleotides or nucleotide analogs are being provided. The invention also contemplates having the polymerase immobilized to the surface.

Various methods can be used to anchor or immobilize the target nucleic acids or the primers to the surface of the substrate. The immobilization can be achieved through direct or indirect bonding to the surface. The bonding can be by covalent linkage. See, Joos et al., Analytical Biochemistry 247: 96-101, 1997; Oroskar et al., Clin. Chem. 42:1547-1555, 1996; and Khandjian, Mole. Bio. Rep. 11:107-115, 1986. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipidic monolayer or bilayer. Other methods for known in the art for attaching nucleic acids to supports also can be used.

When biotin-streptavidin linkage is used to anchor the nucleic acids, the nucleic acids can be biotinylated, while one surface of the substrates can be coated with streptavidin. Since streptavidin is a tetramer, it has four biotin binding sites per molecule. Thus, it can provide linkage between the surface and the nucleic acid. In order to coat a surface with streptavidin, the surface can be biotinylated first, and then one of the four binding sites of streptavidin can be used to anchor the protein to the surface, leaving the other sites free to bind the biotinylated nucleic acid (see, Taylor et al., J. Phys. D. Appl Phys. 24:1443, 1991). Such treatment leads to a high density of streptavidin on the surface of the substrate allowing a correspondingly high density of template coverage. Surface density of the nucleic acid molecules can be controlled by adjusting the concentration of the nucleic acids applied to the surface. Reagents for biotinylating a surface can be obtained, for example, from Vector Laboratories. Alternatively, biotinylation can be performed with BLCPA: EZ-Link Biotin LC-PEO-Amine (Pierce, Cat. 21347), or any other known or convenient method.

In some embodiments, labeled streptavidin of very low concentration (e.g., in the μM, nM or pM range) is used to coat the substrate surface prior to anchoring. This can facilitate immobilization of the nucleic acid with single molecule resolution. It also can allow detecting spots on the substrate to determine where the nucleic acid molecules are attached, and to monitor subsequent nucleotide incorporation events.

Other embodiments of the invention provide for primer/template anchoring methods that reproducibly attach to a surface comprising a nucleic acid with appropriate bioactivity to be sequenced by a single molecule sequencing methodology. When sequencing at the single molecule level, it is important that the template remain as stationary and stable on the substrate as possible. For example, primers and/or templates according to the invention can include a polyA, polyT, polyC, polyU and/or polyG tail. In some embodiments, the primer and/or template can include an average tail length of or greater than about 50 bases (average range of about 10 to about 100+ bases). In other embodiments, the primer and/or template can include an average tail length less than about 50 bases, for example, 5-10 bases on average. It is preferred that the primer and template include tails having different but complementary bases. The homopolymer primer/template slide back and forth until a first base is added which "locks" the alignment of the primer/template in place. Additional bases can be added to further "lock" the alignment of the primer/template.

While different nucleic acid molecules can be each immobilized to and sequenced in a separate substrate, multiple nucleic acids also can be analyzed on a single substrate. In the latter scenario, the templates can be bound to different locations on the substrate. This can be accomplished by a variety of different methods, including hybridization of primer capture sequences to nucleic acids immobilized at different locations on the substrate.

In certain embodiments, different nucleic acids also can be attached to the surface of a substrate randomly as the reading of each individual molecule may be analyzed independently from the others. Any other known methods for attaching nucleic acids and/or proteins may be used.

C. Detection

Any detection method may be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (1995) and Mathies et al. (1992). Hybridization patterns may also be scanned using a CCD camera (e.g., Model TE/CCD512SF, Princeton Instruments, Trenton, N.J.) with suitable optics (Ploem, 1993), such as described in Yershov et al. (1996), or may be imaged by TV monitoring (Khrapko, 1991). For radioactive signals, a phosphorimager device can be used (Johnston et al., 1990; Drmanac et al., 1992; 1993). Other commercial suppliers of imaging instruments include General Scanning Inc., (Watertown, Mass. www.genscan.com), Genix Technologies (Waterloo, Ontario, Canada; www.confocal.com), and Applied Precision Inc. Such detection methods are particularly useful to achieve simultaneous scanning of multiple tag complement regions.

The present invention provides for detection of a single nucleotide into a single target nucleic acid molecule. A number of methods are available for this purpose. Methods for visualizing single molecules within nucleic acids labeled with an intercalating dye include, for example, fluorescence microscopy. For example, the fluorescent spectrum and lifetime of a single molecule excited-state can be measured. Standard detectors such as a photomultiplier tube or avalanche photodiode can be used. Full field imaging with a two-stage image intensified COD camera also can be used. Additionally, low noise cooled CCD can also be used to detect single fluorescent molecules.

The detection system for the signal may depend upon the labeling moiety used, which can be defined by the chemistry available. For optical signals, a combination of an optical fiber or charged couple device (CCD) can be used in the detection step. In those circumstances where the substrate is itself transparent to the radiation used, it is possible to have an incident light beam pass through the substrate with the detector located opposite the substrate from the target nucleic acid. For electromagnetic labeling moieties, various forms of spectroscopy systems can be used. Various physical orientations for the detection system are available and discussion of important design parameters is provided in the art.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photo-conversion, single and/or multiphoton excitation, spectral wavelength discrimination, fluorophore identification, evanescent wave illumination, and total internal reflection fluorescence (TIRF) microscopy. In general, certain methods involve detection of laser-activated fluorescence using a microscope equipped with a camera. It is sometimes referred to as a high-efficiency photon detection system. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use total internal reflection fluorescence (TIRF) microscopy for two-dimensional imaging. TIRF microscopy uses totally internally reflected excitation light and is well known in the art. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. In other words, the optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the immobilized target nucleic acid-primer complex in the presence of a polymerase. Total internal reflection (TIR) fluorescence microscopy is then used to visualize the immobilized target nucleic acid-primer complex and/or the incorporated nucleotides with single molecule resolution.

Measured signals can be analyzed manually or by appropriate computer methods to tabulate results. The substrates and reaction conditions can include appropriate controls for verifying the integrity of hybridization and extension conditions, and for providing standard curves for quantification, if desired. For example, a control primer can be added to the nucleic acid sample for extending a target nucleic acid that is known to be present in the sample (or a target nucleic acid sequence that is added to the sample). The absence of the expected extension product is an indication that there is a defect with the sample or assay components requiring correction.

EXAMPLES

The following Examples 1-12 were conducted to provide exemplary methods and devices for preparing a surface of a substrate for immobilizing a target nucleic acid. Generally, the following Examples 1-12 were conducted to treat a surface of a substrate such that single molecules can be individually optically resolved.

Example 1

Amine-modified oligonucleotides were attached to the aldehyde-modified 'SuperAldehyde'-slides (TeleChem International Inc., Sunnyvale, Calif.; lot numbers 000529 and 000831) according to the protocol given by the manufacturer. The oligonucleotide concentration was 25 µM in 0.5×ArrayIt Micro spotting solution (TeleChem International Inc., Sunnyvale, Calif.). To remove the unbound oligonucleotides after spotting and deactivate the excessive aldehyde groups, the slides were processed as described in the protocol: washed twice in 0.2% sodium dodecyl sulfate (SDS) for 5 minutes each, twice in $dH_2O$ for 5 minutes each and once in a solution containing 0.25 g $Na_2BH_4$ dissolved in 75 ml phosphate-buffered saline (PBS) and 25 ml EtOH for 5 minutes. Additionally the slides were washed three times in 0.2% SDS for 1 minute each and twice in $dH_2O$ for 1 minute each. These slides were denoted 'SuperAldehyde 1'. One modification employed to this protocol involved the incubation of slides in 0.1 M Tris-HCl pH 8.0 with 0.05 M $NaCNBH_3$ and 0.01 M NaOH for 15 minutes. The slides were then washed three times in 0.2% SDS for 1 minute each and once with $dH_2O$. These slides were denoted 'SuperAldehyde 2'. Both 'SuperAldehyde' slides were dried and stored at 20° C.

Example 2

Aminemodified oligonucleotides were attached to the 3D-Link™-slides (SurModics, Inc., Eden Prairie, Minn.) according to the protocol given by the manufacturer. The oligonucleotides were dissolved in 150 mM sodium phosphate buffer pH 8.5 at a 25 µM concentration. After printing the arrays were stored for 4-72 h in a chamber with 75% relative humidity (SurModics, Inc., Eden Prairie, Minn.). The excess amine-reactive groups were deactivated for 15 minutes at 50° C. in a solution containing 50 mM ethanolamine, 0.1 M Tris-HCl pH 9.0 and 0.1% SDS. The slides were washed with $dH_2O$, in a solution containing 4×SSC and 0.1% SDS at 50° C. for 15-60 minutes and finally with $dH_2O$. The slides were stored desiccated at 20° C. until use.

Example 3

Nucleotides attached to mercaptosilane-derivatized slides (Orchid Bioscience, Inc., Princeton, N.J.) were modified with 5' disulfide groups (Operon Technologies, Inc., Alameda, Calif.) and diluted to a concentration of 25 µM in 0.5 M sodium carbonate buffer (pH 9.0) and 0.02% SDS. After spotting, the slides were kept in a chamber with 75% relative humidity for 5 minutes to overnight. The slides were then washed three times with a solution containing 10 mM Tris-HCl pH 7.5, 150 mM NaCl and 0.05% Tween-20. After washing with dH$_2$O the slides were left to dry and stored at 20° C. until use. For attaching acrylamide-modified oligonucleotides (Sigma-Genosys Ltd, Cambridge, UK) to the mercaptosilane-surfaced slides the oligonucleotides were dissolved as for attachment to the EZ-RAYS™-slides (Mosaic Technologies, Waltham, Mass.), see below. The post-spotting procedures were the same as those described for the disulfide-modified oligonucleotides Example 4

Acrylamide-modified oligonucleotides were attached to the EZ-RAYS™-slides according to the Dec. 1, 2000 version of the protocol given by the manufacturer. The oligonucleotides were dissolved in 100 mM sodium carbonate buffer (pH 10.0) containing 0.0008% N-lauroyl-sarcosine to a final concentration of 25 µM. The latent thiol groups on the slides were activated before spotting the oligonucleotides for 15-30 minutes in a solution containing 0.64 g of tris(carboxyethyl) phosphine hydrochloride in 45 ml of dH$_2$O. The slides were briefly washed with dH$_2$O and dried at 20° C., the oligonucleotides were spotted and the arrays were left at 20° C. for at least 60 minutes after arraying. The post-array processing included soaking the arrays for 30 minutes in 40 ml quench buffer containing sodium acrylate (Mosaic Technologies, Waltham, Mass.) and washing the arrays twice for 5 minutes each in 10 mM Tris-HCl pH 8.0 with 1 mM Na$_2$EDTA. Finally, the arrays were rinsed briefly with dH$_2$O. The slides were stored at 20° C. until use. Disulfide-modified oligonucleotides were also attached to the EZ-RAYST™-slides. These oligonucleotides were diluted to a concentration of 25 µM, in a 0.5 M sodium carbonate buffer (pH 9.0) and 0.02% SDS. The post-spotting procedures were the same as those described for attaching the acrylamide-modified oligonucleotides to the EZ-RAYS™-slides Example 5

Silanized oligonucleotides (Interactiva Biotechnologie GmbH, Ulm, Germany) were immobilized to the unmodified glass surface (Menzel-Glaser, Braunschweig, Germany) as described by Kumar et al. with a few modifications. The slides were not washed before spotting since that caused the spots to spread and mix with each other. Finally, the slides were air-dried and stored at 20° C. until use. The concentration of the oligonucleotides was 15 µM and they were dissolved in DMSO/H$_2$O 2:1 (eNOS co) and 1:1 (eNOS nc).

Example 6

The following example provides an exemplary single molecule sequencing method and device using a PEM surface for immobilizing a target nucleic acid.

A fused silica microscope slide (1 mm thick, 25×75 mm size, Esco Cat. R130110) was used to attach DNA templates. The slides were first RCA-cleaned. Glass slides were sonicated in a 2% Micro-90 solution (Cole-Palmer) for 30 minutes. After sonication, the slides were rinsed in a cascading stream of MilliQ water (Millipore) for 8 minutes and stored in MilliQ water after rinsing. The rinsed slides were then boiled in a 50 ml beaker containing a fresh solution of 6:4:1 MilliQ water/NH$_4$OH(28%)/H$_2$O$_2$(30%) at 60 C for 90 minutes. The slides are then rinsed in MilliQ water and stored. The RCA cleaning method is also described in WO 01/32930, incorporated by reference herein.

A multilayer of polyallylamine/polyAcrylic was absorbed to the slide. An EZ link connector was then attached to the slides as follows: the slide was dried, scratched with diamond pencil, and then covered with a hybridization chamber. 120 #1 of a mixture of 1:1:8 EDC:BLCPA:MES (50 mM EDC, 50 mM BLCPA, 10 mM MES) was applied to each slide. Following incubation for 20 minutes, 120 #1 of Streptavidin Plus diluted to 0.1 mg/ml was added to the slide. After 20 minutes of incubation, the slide was washed with 200/µl of Tris 10 µM.

Preparation of 10 pM Oligo: a 7 G nucleic acid template was pre-hybridized with Cy5-labeled primer in TRIS-MgCl2 buffer. The treated slide was examined for contamination with the TIR microscope. 200 #1 of the target nucleic acid/primer mixture was applied to each slide. Following incubation for 10 minutes, the slide was washed with 200/xl ml of Tris 10 mM.

Addition of nucleotides and polymerase: nucleotides dTTP, dATP, dGTP, and Cy3-dCTP, each of 20-100 nM were mixed in the ECOPOL buffer. 1 #1 Klenow 210S from stock solution (kept in −20° C.) was added to 200 microliters of the nucleotide mixture. 120 µl of the mixture was then added on each slide. After incubation for 0 to 30 minutes (for different experiments), the slide was examined with the TIR microscope. Unless otherwise noted, all reactions were performed at room temperature, while the reaction reagents were kept at 4° C. or −20° C. The primer/nucleic acid hybridization reaction was carried out with a thermocycler machine.

Single molecule resolution was achieved by using a low concentration of the nucleic acid template which ensured that only one template molecule is attached to a distinct spot on the slide. Single molecule attachment to a distinct is also confirmed by the observation of single bleaching pattern of the attached fluorophores. In the reaction described above, a concentration of about 10 pM of a 80-mer oligonucleotide template was used for immobilizing to the slide. The space between different DNA molecules attached to the surface slide was measured at a few micrometers.

Imaging with Single Molecule Resolution: As illustrated in FIG. 1, incorporation of a nucleotide molecule into the complementary strand of a target molecule was detected and imaged according to the present invention. FIG. 1 shows two different target nucleic acids analyzed in parallel on the surface of a substrate. Incorporation of, for example, a labeled adenine nucleotide (A*) into a complementary stand of one of the target nucleic acid is visualized on the surface, as indicated by the spot shown in the top view. Later, incorporation of, for example, a labeled thymine nucleotide (T*) into the complementary strand of a different target nucleic acid can be seen as a spot on a different position in the field of view, corresponding to a different location on the surface of the substrate. If nucleotides incorporate into both stands, for example two A*'s, two spots at corresponding positions can be detected, indicating incorporation into the complementary strands of the two individual target nucleic acids.

Figure 2:
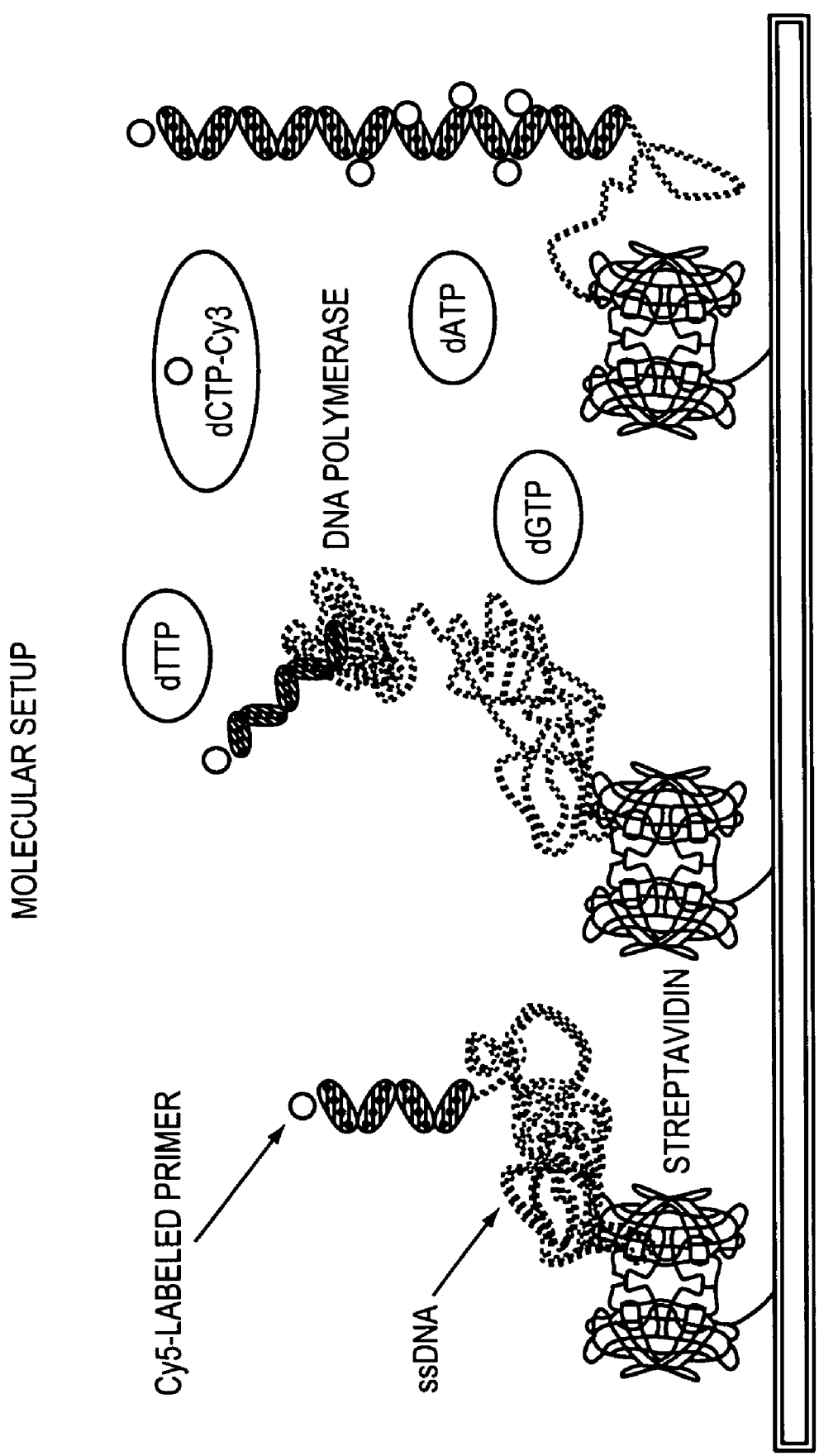
FIG. 2 depicts the molecular set-up for performing single molecule sequencing using a biotin-streptavidin binding pair and Cy3 and Cy5 labels.

As schematically illustrated in FIG. 2, a single-stranded oligonucleotide template primed with a Cy5 labeled primer was immobilized on the surface of a fused silica slide using a biotin-streptavidin. An exemplified scheme of coating a substrate with PEM for immobilizing nucleic acid is provided as follows:

Carboxylic acid groups are negatively charged at pH 7, and are a common target for covalent bond formation. Terminating the surface with carboxylic acid groups generates a surface which is both strongly negatively-charged and chemically reactive. In particular, amines can link to carboxylic acid groups to form amide bonds, a reaction catalyzed, for example, by carbodiimides. Thus, a molecule with biotin at one end, hydrophilic spacer, and an amine at the other end can be used to terminate the surface with biotin.

Streptavidin is capable of converting a biotin-terminated surface to a surface capable of capturing biotin. Streptavidin, which carries a slight negative charge, can be used then to attach the nucleic acid templates to be analyzed to the surface by using a biotinylated primer. A buffer with a high concentration of multivalent salt can be used in order to screen the repulsion of the negatively charged surface for the negatively-charged DNA.

To coat the PEM, glass cover slips can be first cleaned with high purity $H_2O$ ($H_2O$ deionized to 18.3 MOhm-cm and filtered to 0.2 #m) and a RCA Solution (6:4:1 mixture of high purity $H_2O$, (30% $NH_4OH$), and (30% $H_2O_2$)). The cover slips can be then sonicated in 2% Micro 90 detergent for 20 minutes. After thoroughly rinsing with high purity $H_2O$, the cover slips can be stirred in gently boiling RCA solution for at least 1 hour, and rinsed again with high purity $H_2O$.

After cleaning, the glass cover slips can be submerged in PAII solution (Poly(allylamine) (PAII, +): 2 mg/ml in high purity $H_2O$, adjusted to pH 7.0) and agitated for at least 10 minutes. The cover slips can then be removed from PAII and washed with BP $H_2O$ by submerging in BP $H_2O$ with agitation, repeated for at least three times. The treatment can continue by agitation in a PAcr solution (Poly(acrylic acid) (PAcr, −): 2 mg/ml in high purity $H_2O$, adjusted to pH 7.0) for at least 10 minutes and washed with high purity $H_2O$. The treatment steps can then be repeated once.

After PEM coating, the PEM coated glass can be incubated with an EDC/BLCPA solution for 30 minutes. The EDC/BLCPA solution can be prepared by mixing equal amounts of 50 mM EDC solution (in MES buffer) and 50 mM BLCPA (in MES buffer) and diluting to 5 mM in MES buffer. The glass can then be rinsed with 10 mM Tris-NaCl and incubated with 0.1 mg/ml streptavidin solution for 1 hour. After washing with 10 mM Tris-NaCl, the glass can be incubated with a solution containing the nucleic acid template (for example, 10−7 M in Tris 100 mM $MgCl_2$) for 30 minutes. The glass can be again rinsed thoroughly with 10 mM Tris-NaCl.

For in-situ attachment, the microfluidic substrate can be bonded to the glass cover slip by HCl-assisted bonding. Essentially, the chips can be first washed with a surfactant (e.g., first with high purity $H_2O$, then in 0.1% Tween 20, then rinsed again with high purity $H_2O$). The washed microfluidic chips can then be put on the glass cover slips with a few microliters of dilute HCl (e.g., 1% HCl in high purity $H_2O$), followed by baking at 37° C. for 1-2 hours. Such treatment can enhance the bond strength to glass (e.g., >20 psi pressure) without increasing nonspecific adsorption.

Following HCl treatment, PEM formation, biotinylation, and streptavidinylation, template attachment can be performed using essentially the same reagents and methods as described above for ex-situ attachment, except that the solutions can be injected through the channels by pressure instead of just being aliquoted onto the substrate surface.

The surface was coated with biotin as follows. A 50 mM solution of 1-[3-(dimethylamino)propyl]-3-ethylcarbodiimide hydrochloride (EDC) was prepared in 2-[N-morpholino]ethanesulfonic acid) (MES) buffer (48 mg of EDC in 2.5 ml MES buffer). A 5 ml aliquot of the EDC solution was then combined with biotin-LC-PEO amine solution (50 mg Biotin-Lc-PEO in 2.5 ml MES buffer) to make an EDC-biotin solution. The solution was diluted in MES buffer to a total volume of 96 ml. The polyelectrolyte multilayer coated slides were then immersed in the EDC-biotin solution in a 100 ml beaker for 60 minutes at room temperature. The slides were then rinsed in MES with gentle agitation for 10 seconds. The rinse was then repeated further with clean 100 ml volumes. The slides were then rinsed in 5 clean volumes of 3×SSC-0.1% triton buffer. Slides were incubated for 10 minutes in the final rinse with the 3×SSC-0.1% triton buffer. Finally, the slides were agitated in a 10 mM Tris-NaCl buffer (10 mM Tris-HCL/10 mM NaCl) for 10 minutes. The resulting slides had a uniform biotin layer.

A layer of streptavidin was next added to the slides. A 14 mg/ml solution of Streptavidin-Plus (SA20, Prozyme) was dissolved in 10 mM Tris/10 mM NaCl buffer by stirring for 10 minutes at room temperature. The solution was filtered with a 0.2 u filter. Biotinylated slides were immersed in the streptavidin solution in a 100 ml beaker and stirred using a stir bar for 15 minutes at room temperature. The slides were rinsed in 100 ml of the 10 mM Tris/10 mM NaCl buffer with gentle agitation for 10 seconds. Rinsing was then repeated in 5 clean 100 ml volumes of 3×SSC-0.1% Triton, allowing the slides to incubate in the final solution for 10 minutes. The slides were then transferred to a fresh bath of 10 mM Tris-NaCl and agitated for 10 seconds. The resulting streptavidinated slides were stored submerged in 10 mM Tris-NaCl at 4° C. prior to use.

Oligonucleotide template, with a biotin molecule attached to one of its ends, was able to attach to the streptavidin-linked surface. The slide surface was negatively charged which aids in repelling unbound nucleotides. The DNA is specifically attached to the surface by its 5' side, meaning that the primer—which the polymerase extends—is away from the surface.

Figure 3:
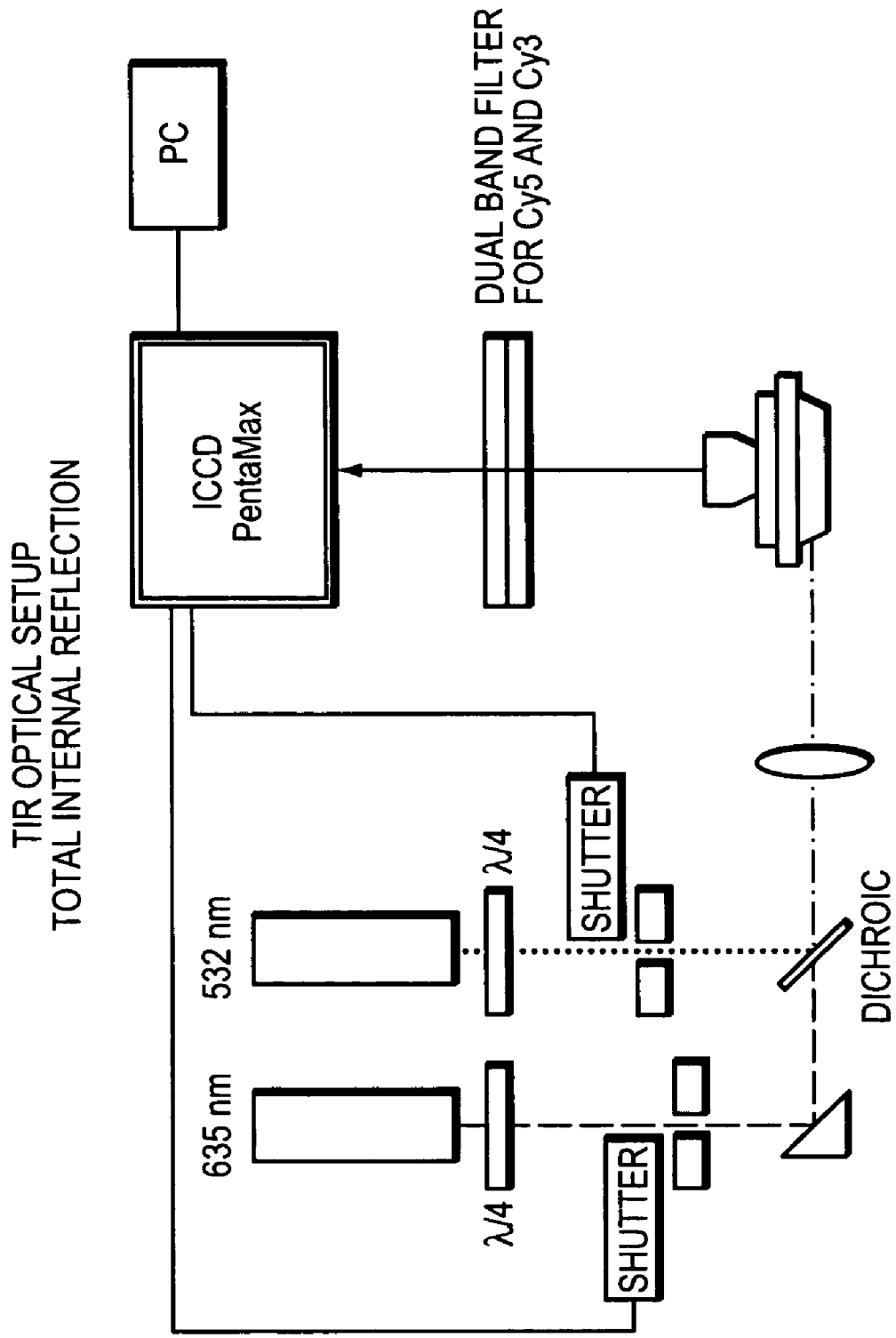
FIG. 3 depicts total internal reflection optical set up for single molecule sequencing.

The template and incorporation of labeled nucleotides were visualized by fluorescence imaging. Location of the oligonucleotide was monitored by fluorescence from the Cy5 labeled primer. Incorporation of nucleotides was detected because the nucleotides were labeled with Cy3. After incorporation, the incorporated labels were illuminated. Illumination of Cy3 was at a wavelength of 532 µm. Following a typical time of a few seconds of continued illumination, the signals were bleached, typically in a single step. As shown in FIG. 3, imaging of fluorescent signals with single molecule resolution was enabled with surface illumination by total internal reflection (TIR).

The following is an exemplary method for directly linking a nucleic acid template to a substrate comprising an epoxide.

Direct Linkage

Figure 4A:
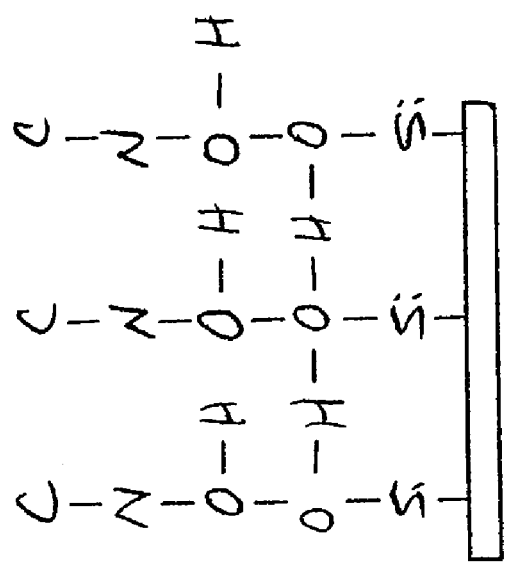
FIGS. 4A and 4B depict exemplary schemes for directly and indirectly linking a template nucleic acid to a substrate comprising an epoxide.
Figure 4A:
Figure 4A:
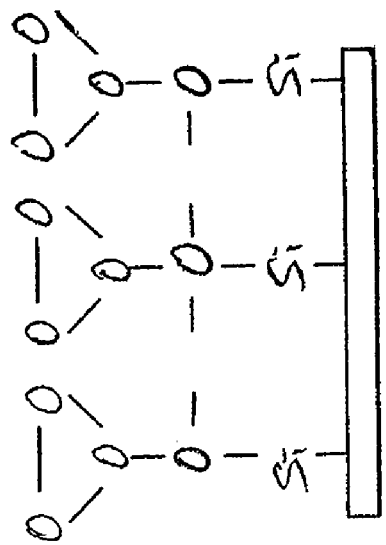

An epoxide molecule 6 was linked to a surface 2 as shown in FIG. 4A. Any molecule or group of molecules capable of binding an epoxide molecule 6 to a surface of a substrate 2, such as a silicon group 4, may be used as a linker. An amine-derived nucleic acid template (IDT) 26 was directly linked via the amine group 32 to the epoxide residue 30. The substrate 2 was then passivated with Tris at 30° C.-40° C. for 1 hour. The nucleic acid template 26 was then sequenced according to methods described herein. Exemplary sequencing methods are provided, for example, in Example 12

Indirect Linkage

Figure 4B:
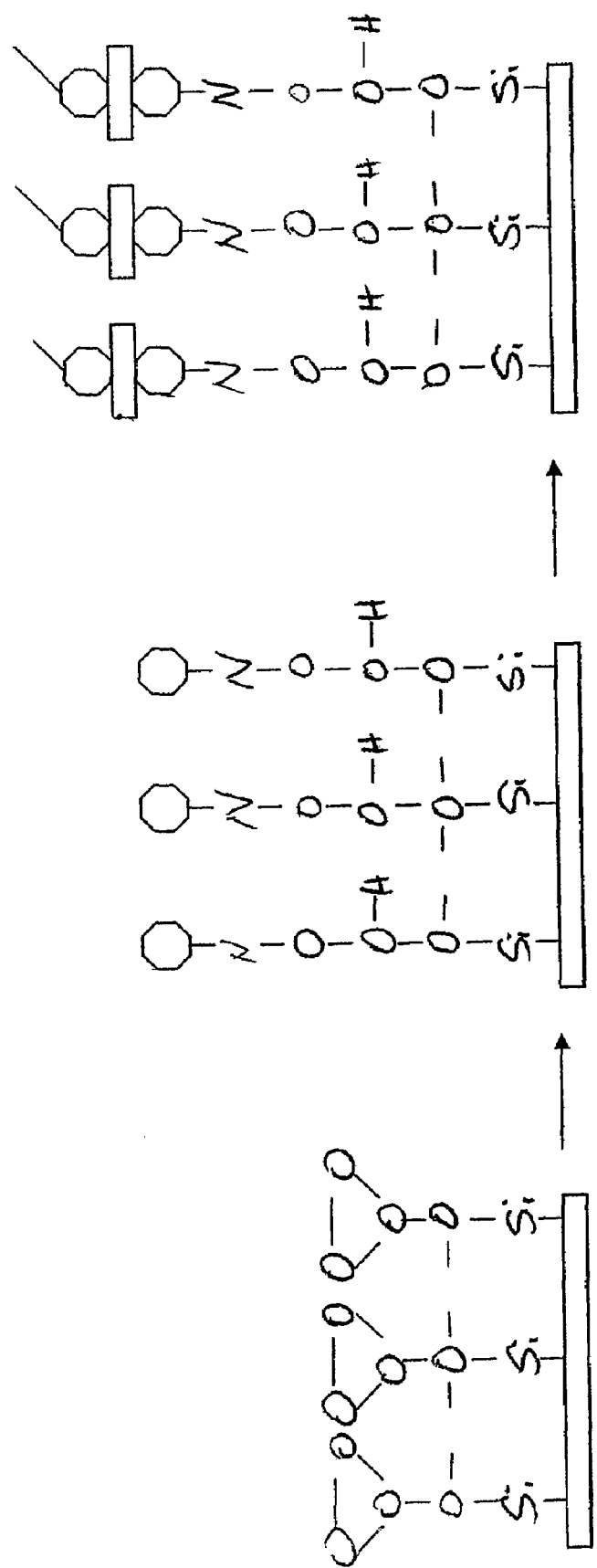

An epoxide molecule 6 was linked to a surface of a substrate 2 as shown in FIG. 4B. Any molecule or group of molecules capable of binding an epoxide molecule 6 to a surface of a substrate 2, such as a silicon group 4, may be used as a linker. A biotinylated amine 20 was added to react with or break the epoxide molecule 6 and bind to the epoxide residue 30. Streptavidin 34 was then added to the surface of the substrate 2, thereby attaching the streptavidin 34 to the available biotinylated amine 20. A biotinylated nucleic acid template 24 was then added to the surface of the substrate 2 and bound to the streptavidin 32. Sequencing of the nucleic acid template 26 was then performed according to the methods described herein. Exemplary sequencing methods are provided, for example, in Example 12.

Example 8

Figure 5:
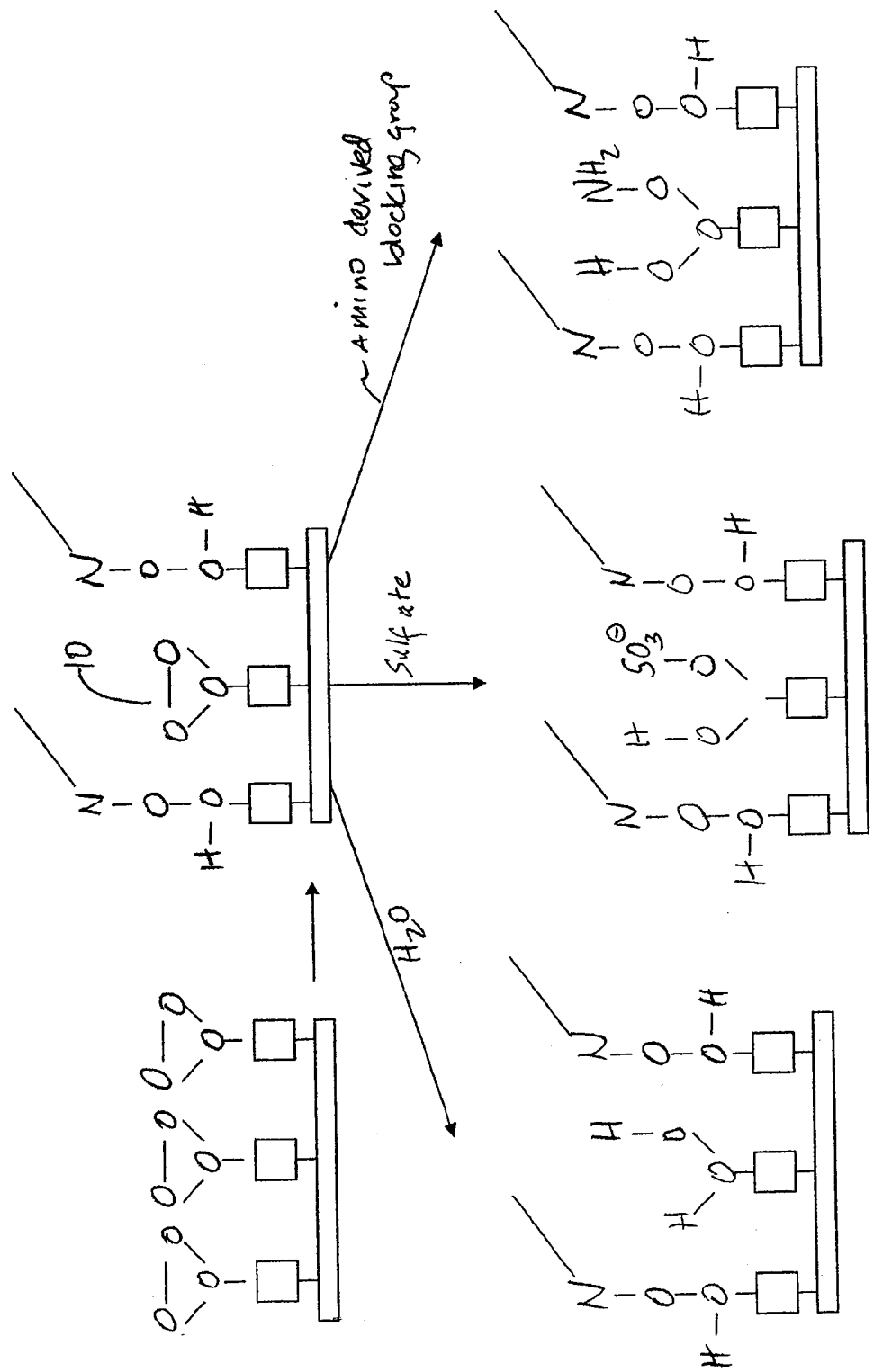
FIG. 5 depicts an exemplary scheme for blocking a substrate comprising an epoxide thereby inhibiting non-specific binding of molecules to the substrate.

The following describes exemplary blocking methods according to the invention. As shown in FIG. 5, a substrate 2 comprises an epoxide molecule 6 linked to its surface by a linker 38 capable of securing the epoxide molecule 6 to the surface of the substrate 2. In this embodiment, an amine-derived nucleic acid template 26 was directly attached to the epoxide residue 30 via the amine group 32 of the nucleic acid template 26. However, an unbound epoxide molecule 10 may still be available on the substrate 2. As discussed herein, an unbound epoxide molecule 10 is highly reactive and may interact with any reagents (e.g., primers, unincorporated nucleotides, labels, polymerases) that create background which interferes during nucleic acid sequencing reactions.

In order to block epoxide molecules that not bound to template nucleic acids, water 12, sulfate 14, or an amine-derived blocking group 16, can be added alone or in combination. Other blocking agents can also be used alone or in combination with water 12, sulfate 14, or an amine-derived blocking group 16 (e.g., a detergent such as Tris). Methods for blocking epoxide coated surfaces using water 12, sulfate 14, an amine-derived blocking group 16, a phosphate ($PO_4$) or a detergent, were performed on surfaces where the template nucleic acid was linked to the epoxide group using direct and indirect linking scheme as described in Example 7.

Example 9

Figure 6:
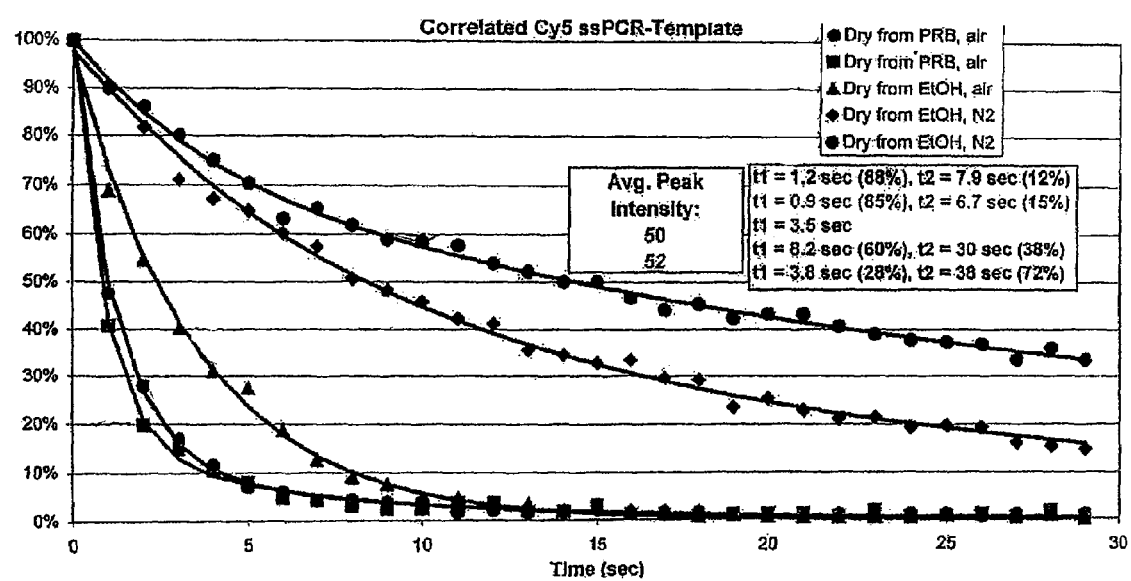
FIG. 6 provides a chart showing increased resolution of incorporation events resulting from exposing a surface comprising an epoxide to various drying agents.

The following provides exemplary image drying methods facilitating the detection of nucleic acid incorporation using a surface comprising an epoxide. In order to increase resolution of label on an epoxide surface, the following protocol was performed. In a surface comprising an epoxide blocked with phosphate ($PO_4$). sequencing reactions were conducted using a Cy3-labeled poly T primer that was hybridized to Cy5 ssPCR template and amplified by PCR. Thereafter, the surface was exposed to a drying agent, such as phosphate rinse buffer. The reactions were done in real time. The surface was dried out from PRB by passing or exposing the surface to air. Additional step included exposing the surface to an additional drying agent (50 µl of EtOH) to further dry out the surface. Even additional steps included exposing the surface to a $N_2$ cylinder, by flowing $N_2$ backwards through a flowcell. The PRB was used to dry out surface dim and bleached within 1 second. Images were taken of the surface during between and during successive "drying" steps. As indicated in FIG. 6, each successive drying event resulted in increased resolution of incorporation events.

Example 10

Figure 7:
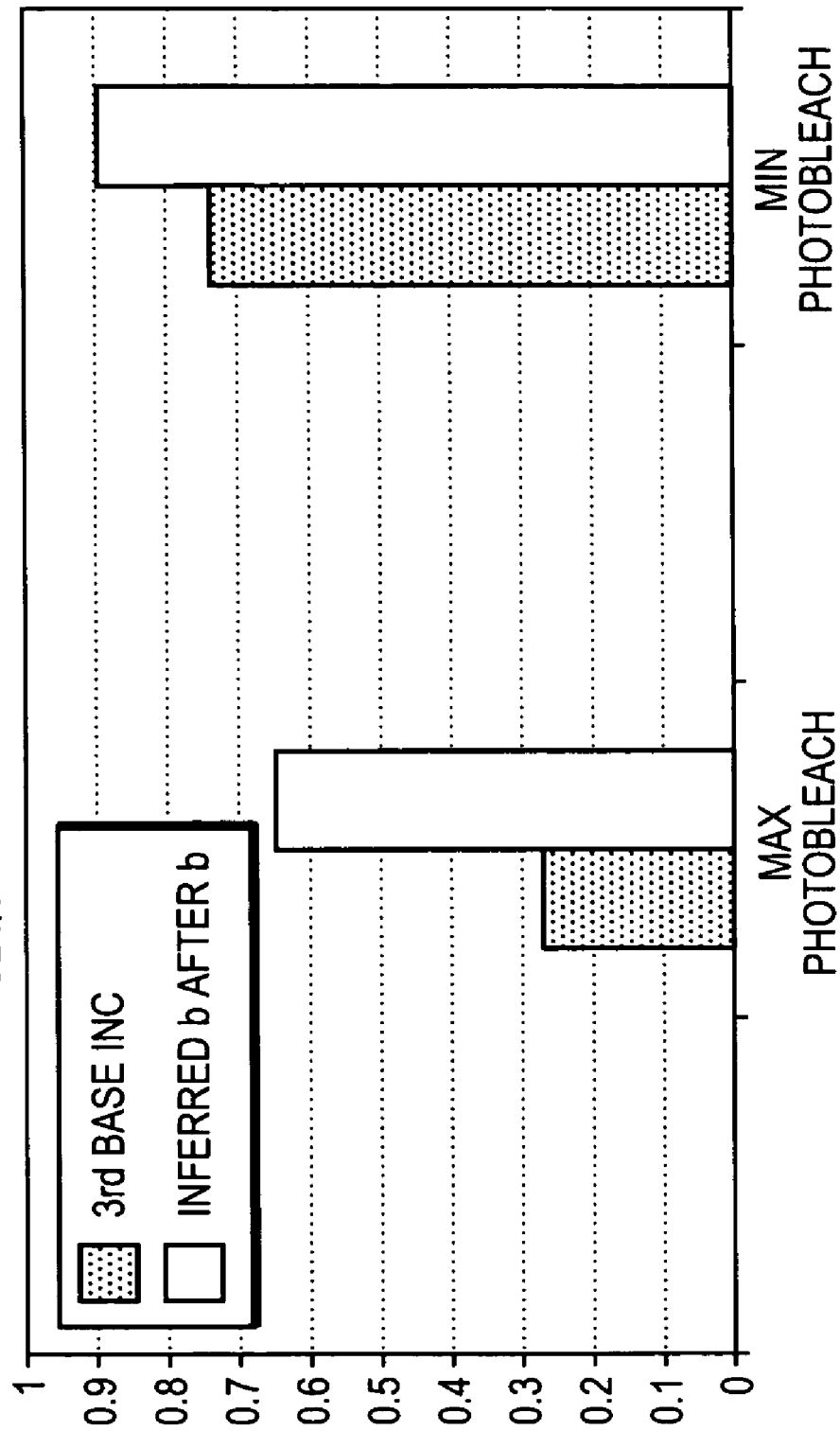
FIG. 7 provides a chart showing the effect of photobleaching on sequencing of a target nucleic acid.

The following experiment was conducted to determine the effect of photobleaching on fidelity of incorporating sequential nucleotides during sequencing. This experiment revealed that reduced photobleaching preserved the integrity of nucleic acids during sequencing. As provided in FIG. 7, under maximum bleach conditions, both $1^{st}$ base (C) and $2^{nd}$ base (G) were subject to 300 seconds photobleaching by green laser. Then a $3^{rd}$ base (A) was imaged with red laser. On the other hand, under minimum bleach conditions, no photobleaching was performed on the first two bases (C) and (G). The $3^{rd}$ base (A) was imaged with red laser.

As indicated in this Figure, base after base efficiencies can be inferred from the $3^{rd}$ base (A) over template efficiency by the third incorporation. Roughly one/third ($\frac{1}{3}^{rd}$) of the molecules stalled due to photobleaching (0.9-0.6).

Example 11

The following experiments were conducted to determine whether certain primer/template anchoring methods were able to reproducibly attach to a surface having a nucleic acid with appropriate bioactivity to be sequenced by a single molecule sequencing methods according to the invention. When sequencing at the single molecule level, it is desired that the template remain as stationary and stable on the substrate as possible.

Following nucleic acid isolation and fragmentation to desired size and repair of fragments generated (using, for example, an enzyme such as PNK to remove 3' phosphates and add 5' phosphates, coupled with limited DNase I treatment as necessary), the fragments were tailed with TdT and dATP to produce an average tail length of 50 bases (average range of 10 to 100+). If necessary, remaining dATP was removed. Second, the material is tailed with TdT and dCTP to provide an average tail length a homopolymer much shorter than produced in the first step, for example, 5-10 bases on average. Although, tailing was first done with dATP and followed with dCTP, sequential tailing can be accomplished with any two different bases and it is not important to the invention which two of four bases are utilized during the process.

The surface contained capture oligonucleotide (5'-attached, direct covalent or via a binding pair such as biotin:streptavidin, and free 3'-OH) with a sequence that is at least partially complementary to the tails produced earlier. The object of this step is to force an alignment point between the random length generated homopolymer tail on the target nucleic acid to that provided attached on the surface. The homopolymer primer/template slide back and forth until a first base is added which "locks" the alignment of the primer/template in place. Additional bases can be added to further "lock" the alignment of the primer/template.

Following hybridization, any unevenness in length of the hybrids was filled in using minimal dTTP and a polymerase with proof-reading activity, preferably Klenow exo+. Optionally, from 1 to 3 dNTPs can be used to fill in the hybrids to maximize the Tm. For example, if dTTP, dGTP and dCTP were the based used, the next base to be added should be dATP. As such, the actual sequencing reactions should be served with a known base "A". The exo+activity of the polymerase ensures that during the fill in reaction, a base is not added on the 3'-end, which is not properly base paired with the template thus preventing the next base addition. However, it is possible to use a mutant polymerase with exo−. FIG. 8 provides a schematic diagram of an exemplary primer:template anchoring system and method according to the invention.

Example 12

Nucleic acid sequencing reactions may be carried out on template nucleic acids attached to epoxide-coated surfaces as described in the Examples above. Before sequencing, a primer must be selected and annealed to the template. Annealing the primer to the template can occur before or after the template is attached to the epoxide surface. The annealing reaction is performed under conditions that are stringent enough to promote sequence specificity, yet sufficiently permissive to allow formation of stable hybrids at an acceptable rate.

If part of the region downstream of the sequence to be analyzed is known, a specific primer can be constructed and hybridized to this region of the target nucleic acid. Alternatively, if sequences of the downstream region on the target nucleic acid are not known, universal (e.g., uniform) or random primers may be used in random primer combinations. In yet another approach, nucleic acid may be digested with a restriction endonuclease, and primers designed to hybridize with the known restriction sites that define the ends of the fragments produced.

Once target nucleic acid is immobilized on the substrate and hybridized to a primer to form a target nucleic acid-primer complex, primer extension can be conducted to sequence the target nucleic acid or primer using a polymerase and a nucleotide (e.g., dATP, dTTP, dUTP, dCTP and/or a dGTP) or a nucleotide analog. Incorporation of a nucleotide or a nucleotide analog and their locations on the surface of a substrate can be detected with single molecule sensitivity according to the invention. As such, the nucleic acid-primer complex can be individually resolvable. In some aspects of the invention, single molecule resolution can be achieved by anchoring a target nucleic acid at a low concentration to a substrate, and then imaging nucleotide incorporation proceeds, for example, with total internal reflection fluorescence microscopy.

During primer extension, the primer/template complex is exposed to a polymerase, and at least one nucleotide or nucleotide analog allowing for extension of the primer. Also, a nucleotide analog can be modified to remove, cap or modify the 3' hydroxyl group. As such, in certain embodiments, methods of the invention can include, for example, the step of removing the 3' hydroxyl group from the incorporated nucleotide or nucleotide analog. By removing the 3' hydroxyl group from the incorporated nucleotide in the primer, further extension is halted or impeded. In certain embodiments, the modified nucleotide can be engineered so that the 3' hydroxyl group can be removed and/or added by chemical methods. In addition, a nucleotide analog can be modified to include a moiety that is sufficiently large to prevent or sterically hinder further chain elongation by interfering with the polymerase, thereby halting incorporation of additional nucleotides or nucleotide analogs. Subsequent removal of the moiety, or at least the sterically-hindering portion of the moiety, can concomitantly reverse chain termination and allow chain elongation to proceed. In some embodiments, the moiety also can be a label. As such, in those embodiments, chemically cleaving or photocleaving the blocking moiety may also chemically-bleach or photo-bleach the label, respectively.

Methods according to the invention provide for the determination of the sequence of a single molecule, such as a single-stranded target nucleic acid. Generally, target nucleic acids can have a length of about 5 bases, about 10 bases, about 20 bases, about 30 bases, about 40 bases, about 50 bases, about 60 bases, about 70 bases, about 80 bases, about 90 bases, about 100 bases, about 200 bases, about 500 bases, about 1 kb, about 3 kb, about 10 kb, or about 20 kb and so on. Preferred methods of the invention provide for a sequencing and detection system directed towards non-amplified and/or non-purified target nucleic acid sequences.

Methods of the invention also include detecting incorporation of the nucleotide or nucleotide analog in the primer and, repeating the exposing, conducting and/or detecting steps to determine a sequence of the target nucleic acid. A researcher can compile the sequence of a complement of the target nucleic acid based upon sequential incorporation of the nucleotides into the primer. Similarly, the researcher can compile the sequence of the target nucleic acid based upon the complement sequence. The primer selected to attach to the template can also include a detectable label. As described herein, any detection method may be used which is suitable for the type of label employed.

The methods according to the invention can provide de novo sequencing, sequence analysis, DNA fingerprinting, polymorphism identification, for example single nucleotide polymorphisms (SNP) detection, as well as applications for genetic cancer research. Applied to RNA sequences, methods according to the invention also can identify alternate splice sites, enumerate copy number, measure gene expression, identify unknown RNA molecules present in cells at low copy number, annotate genomes by determining which sequences are actually transcribed, determine phylogenic relationships, elucidate differentiation of cells, and facilitate tissue engineering. The methods according to the invention also can be used to analyze activities of other biomacromolecules such as RNA translation and protein assembly. Certain aspects of the invention lead to more sensitive detection of incorporated signals and faster sequencing.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

We claim:

1. A method for conducting a chemical reaction on a surface, the method comprising the steps of:
   attaching a plurality of first nucleic acid molecules via covalent linkages to reactive chemical groups on a surface;
   blocking the surface using a blocking solution comprising potassium phosphate;
   conducting a chemical reaction between said first nucleic acid molecules and second reactant molecules comprising an optically detectable label wherein said conducting step comprises exposing said nucleic acid to a primer under conditions sufficient to extend said nucleic acid by at least one base;
   rinsing unincorporated optically labeled nucleotides from the surface; and
   observing individually optically resolvable labels incorporated in the one or more first nucleic acids on the surface.

2. The method of claim 1, wherein said first nucleic acids are DNA or RNA.

3. The method of claim 1, wherein said optically detectable label is a fluorescent molecule.

4. The method of claim 3, wherein said fluorescent molecule is selected from the group consisting of Cyanine-3 and Cyanine-5.

5. The method of claim 1, wherein the reactive chemical groups are epoxide groups.

6. The method of claim 1, wherein the first nucleic acid molecules are attached to the reactive chemical groups indirectly by means of a biotin-streptavidin binding pair wherein biotin is covalently attached to the surface.

7. The method of claim 1, further comprising the step of exposing the surface to a drying agent.

8. The method of claim 7, wherein said drying agent is PRB, EtOH, air or $N_2$.

9. The method of claim 1, further comprising determining nucleic acid sequences of one or more of the first nucleic acid molecules.

10. The method of claim 9, wherein said determining step comprises conducting sequencing by synthesis.

11. The method of claim 1, wherein the surface comprises a silica coating containing exposed epoxide groups.

12. The method as in claim 1, wherein pH of the blocking solution is 8.5.

13. A method for conducting a chemical reaction on a surface, the method comprising the steps of:
   attaching a plurality of first nucleic acid molecules via covalent linkages to reactive chemical groups on an analytical surface;
   blocking the surface using a blocking solution comprising potassium phosphate;
   conducting a chemical reaction using second reactant molecules comprising an optically detectable label thereby incorporating said second reactant molecules;
   rinsing unincorporated optically labeled second reactant molecules from the surface; and
   observing individually optically resolvable labels on the surface.

* * * * *